(12) United States Patent
Lin et al.

(10) Patent No.: US 12,186,223 B2
(45) Date of Patent: Jan. 7, 2025

(54) WEARABLE INTERFACE FOR INTELLIGENT HEALTH PROMOTION SERVICE SYSTEM

(71) Applicant: aiFree Interactive Technology CO., LTD., Tainan (TW)

(72) Inventors: Yang-Cheng Lin, Tainan (TW); Chien-Hsiang Chang, Kaohsiung (TW); Pin-Jun Chen, Kaohsiung (TW); Pei-Yun Wu, Taichung (TW); Wei-Chih Lien, Tainan (TW); Peng-Ting Chen, Tainan (TW)

(73) Assignee: aiFree Interactive Technology CO., LTD., Tainan (TW)

( * ) Notice: Subject to any disclaimer, the term of this patent is extended or adjusted under 35 U.S.C. 154(b) by 826 days.

(21) Appl. No.: 17/334,841

(22) Filed: May 31, 2021

(65) Prior Publication Data
US 2021/0378853 A1 Dec. 9, 2021

Related U.S. Application Data

(60) Provisional application No. 63/036,969, filed on Jun. 9, 2020.

(51) Int. Cl.
| | | |
|---|---|---|
| *A61F 5/01* | (2006.01) | |
| *A61B 5/00* | (2006.01) | |
| *A61F 5/30* | (2006.01) | |

(52) U.S. Cl.
CPC .......... *A61F 5/0125* (2013.01); *A61B 5/0022* (2013.01); *A61F 5/30* (2013.01);
(Continued)

(58) Field of Classification Search
CPC .. A61F 5/0123; A61F 5/30; A61F 5/01; A61F 5/042; A61F 5/0102; A61F 5/0585;
(Continued)

(56) References Cited

U.S. PATENT DOCUMENTS

| | | |
|---|---|---|
| 11,311,228 B1 | 4/2022 | Oakley et al. |
| 2014/0163444 A1 | 6/2014 | Ingvarsson et al. |
| | (Continued) | |

FOREIGN PATENT DOCUMENTS

| | | |
|---|---|---|
| CN | 109464273 A | 3/2019 |
| CN | 105263408 B | 8/2019 |
| | (Continued) | |

OTHER PUBLICATIONS

Translation of DE 19817628 A1; Prinz et al.; 1999 (Year: 1999).*

*Primary Examiner* — Alireza Nia
*Assistant Examiner* — Daniel A Miller
(74) *Attorney, Agent, or Firm* — ScienBiziP, P.C.

(57) ABSTRACT

A wearable device an intelligent health promotion service system (IHPSS) is disclosed. One embodiment of the wearable device (10) is configured to interface plurality groups of skin-mounted sensor pads (130) over a body part (140) of a wearer, and comprises: a modular brace (110) structurally separated from the sensor pads, and a plurality of sensor modules (120). The modular bracing is provided with a plurality groups of orienting slots (111) arranged thereon configured to maintain intra-group orientation between the sensor pads, and is configured to allow inter-group distance adjustment between the groups of the sensor pads over the body part of the wearer. The plurality of sensor modules is configured to be detachably coupled to the groups of sensor pads through the orienting slots in the modular bracing member. The sensor modules are provided with physiological sensing circuits wirelessly communicative with the intelligent health system.

20 Claims, 14 Drawing Sheets

(52) U.S. Cl.
CPC ............... *A61B 2562/0219* (2013.01); *A61B 2562/0247* (2013.01); *A61B 2562/029* (2013.01); *A61F 2005/0188* (2013.01)

(58) Field of Classification Search
CPC .... A61F 5/0104; A61F 5/0106; A61F 5/0109; A61F 5/0022; A61F 2005/0188; A61F 2005/0176; A61F 2/58; A61F 2/581; A61F 2/582; A61F 2/583; A61F 2/585; A61F 2/60; A61F 2/604; A61F 2/605; A61F 2/64; A61F 2/642; A61F 2/644; A61F 2/646; A61F 2/66; A61F 2/6607; A61F 2002/543; A61F 2002/546; A61F 2002/607; A61F 2002/608; A61F 2002/648; A61F 2002/6642; A61F 2002/6664; A61F 2002/6671; A61F 2002/6678; A61F 2002/6685; A61F 2002/6692; A61B 5/0022; A61B 5/11; A61B 5/00; A61B 5/0531; A61B 5/0205; A61B 5/024; A61B 5/0024; A61B 5/02158; A61B 2562/0219; A61B 2562/0247; A61B 2562/029; A61H 1/0274; A61H 1/0277; A61H 1/0281; A61H 1/0237; A61H 1/024; A61H 1/0255
USPC .......................................................... 602/26
See application file for complete search history.

(56) References Cited

U.S. PATENT DOCUMENTS

| | | |
|---|---|---|
| 2014/0213874 A1 | 7/2014 | Tong et al. |
| 2015/0265834 A1 | 9/2015 | Glukhovsky et al. |
| 2015/0366504 A1 | 12/2015 | Connor et al. |
| 2016/0345947 A1 | 12/2016 | Salahieh et al. |
| 2017/0100300 A1 | 4/2017 | Rapp et al. |
| 2017/0224520 A1 * | 8/2017 | Karasahin ............... A61B 5/11 |
| 2017/0258662 A1 * | 9/2017 | Armbrust ............... A61C 7/14 |
| 2019/0209884 A1 * | 7/2019 | Buskila ............. A63B 21/4017 |
| 2020/0121485 A1 | 4/2020 | McDaid et al. |
| 2021/0202800 A1 | 7/2021 | Jung et al. |
| 2022/0104960 A1 * | 4/2022 | Cassit ................ A61B 5/6812 |

FOREIGN PATENT DOCUMENTS

| | | | |
|---|---|---|---|
| CN | 209316800 U | 8/2019 | |
| DE | 19817628 A1 * | 11/1999 | ......... A61F 5/0104 |
| JP | 2009518057 A | 5/2009 | |
| JP | 2012516719 A | 7/2012 | |
| JP | 201583212 A | 4/2015 | |
| JP | 2016515887 A | 6/2016 | |
| JP | 2017515515 A | 6/2017 | |
| WO | 2014153033 A2 | 9/2014 | |
| WO | 2017071785 A2 | 5/2017 | |
| WO | 2020152682 A1 | 7/2020 | |

* cited by examiner

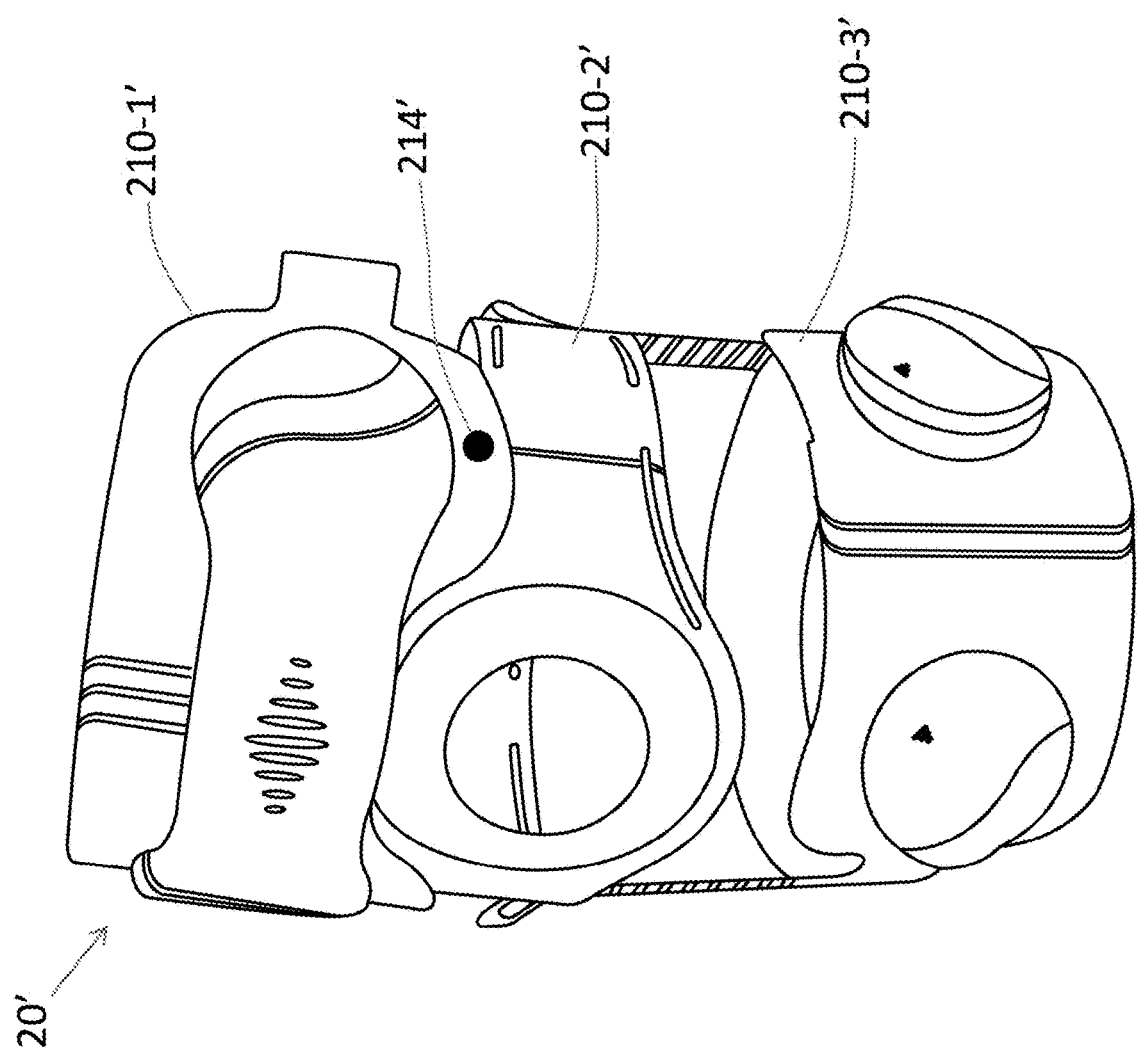

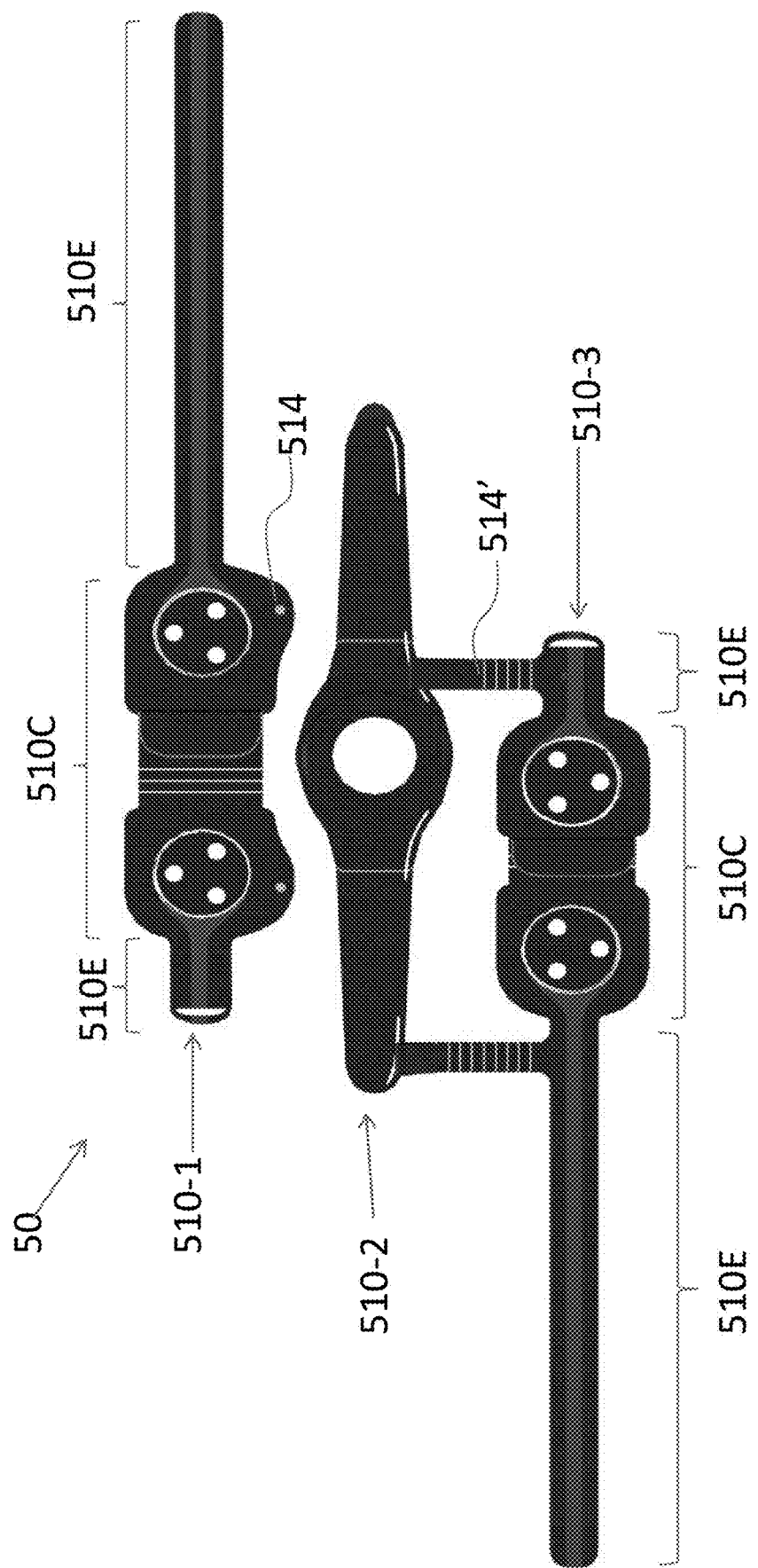

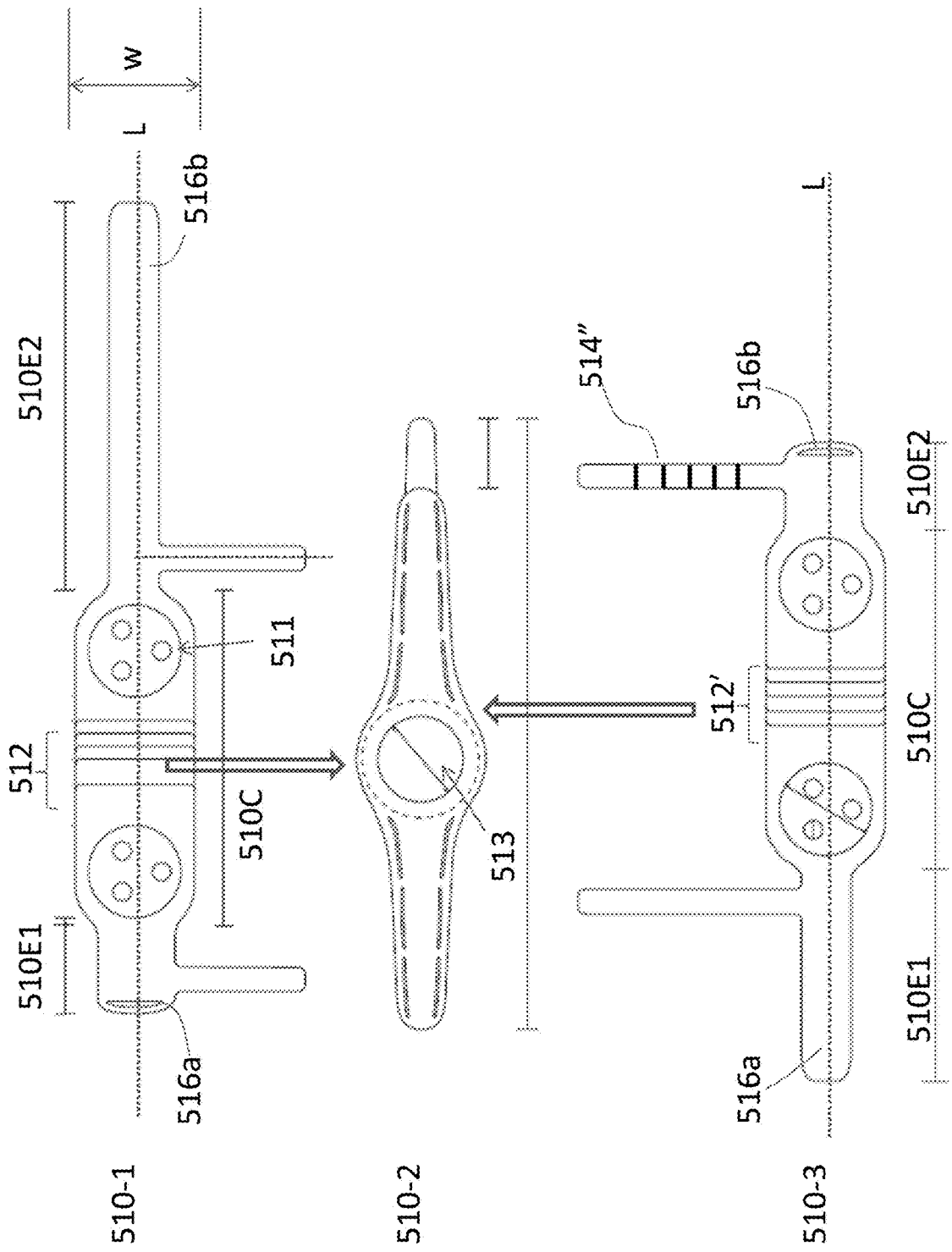

WEARABLE INTERFACE FOR INTELLIGENT HEALTH PROMOTION SERVICE SYSTEM

CROSS-REFERENCES TO RELATED APPLICATIONS

This application claims the benefit of U.S. Provisional Patent Application No. 63/036,969, which is hereby incorporated by reference herein and made as part of specification.

BACKGROUND

1. Field

The present disclosure generally relates to wearable devices, and more specifically to a modular brace system capable of providing therapeutic relief while offering precision retaining capability for positioning~various modular add-on devices over a wearer's body.

2. Related Art

With the advent of an aging society, the number of rehabilitation patients and sub-health groups is increasing, and the demand and scale of the health promotion market is growing rapidly. Rehabilitation groups are in particularly need for routine rehabilitation activities in order to retain and regain physical health.

A great variety of orthotic devices are available on the market or through healthcare prescription. The nature of these orthotic devices range from preventive/augmentation aids for those who are otherwise healthy, to therapeutic constrains that actively induce stabilization for those that have lost varying degrees of self-sustainability and mobility. Regardless of the specific applications, these supplemental wearable devices are frequently used over different parts of a body for varying purposes among users of different conditions.

As these wearable devices have become widely received among the population, it would be beneficial to design a modular wearable interface with application flexibility in mind, whose overall construction comprises generally pliant characteristics without being overly rigid, at the same time being adaptable as a functional device carrier over a body part of a wearer, so as to provide a multi-functional interface for the user in need.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

FIGS. 2A and 2B illustrate embodiments of wearable interface devices in accordance with some embodiments of the present disclosure from a frontal aspect view.

FIGS. 5A and 5B illustrate exemplary modular brace members in an unwrapped configuration in accordance with some embodiments of the instant disclosure.

DETAILED DESCRIPTION

Figure 1:
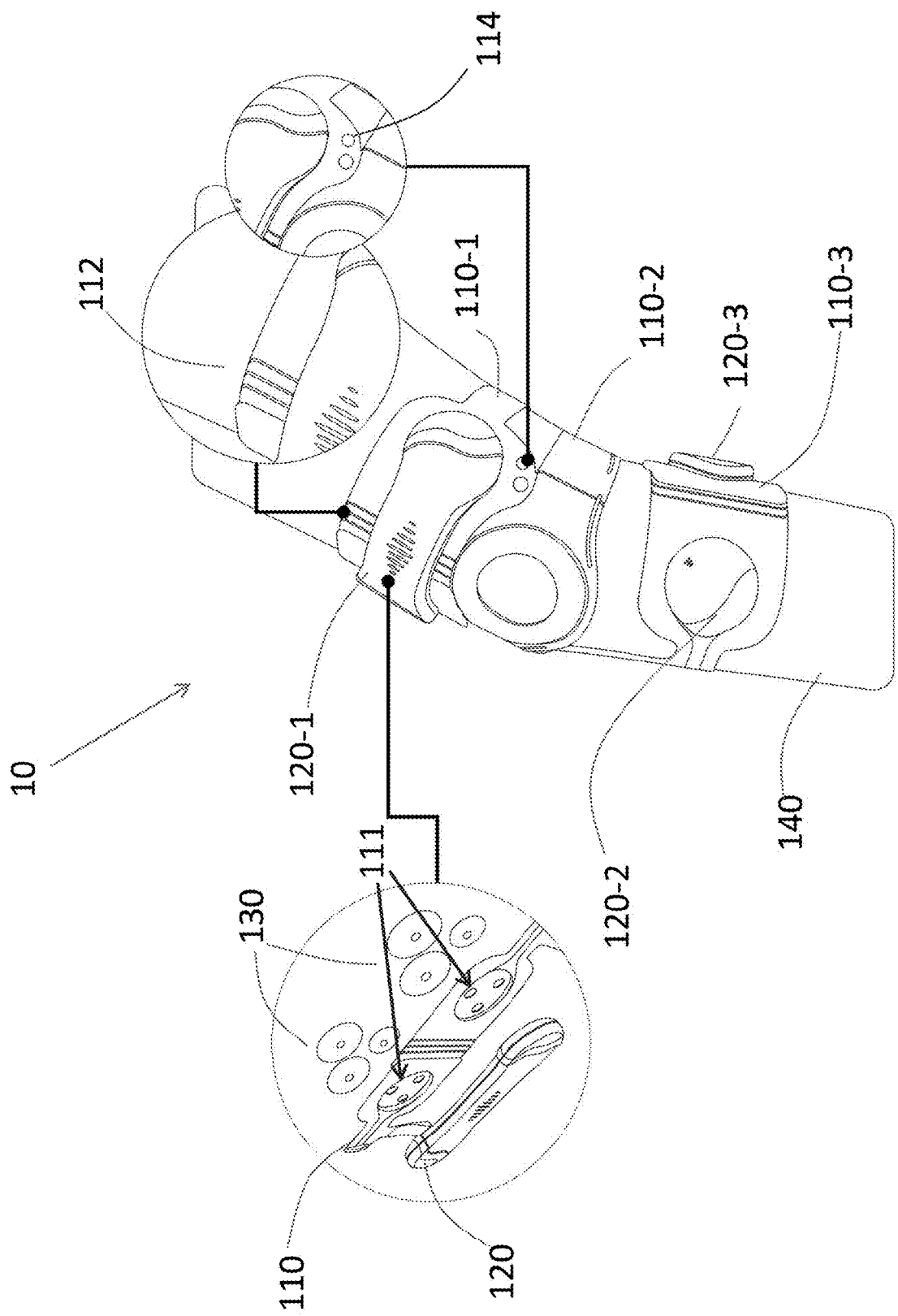
FIG. 1 illustrates a multi-purpose modular wearable interface according to some embodiments of the present disclosure.

The present disclosure will now be described more fully hereinafter with reference to the accompanying drawings, in which exemplary embodiments of the disclosure are shown. This disclosure may, however, be embodied in many different forms and should not be construed as limited to the exemplary embodiments set forth herein. Rather, these exemplary embodiments are provided so that this disclosure will be thorough and complete, and will fully convey the scope of the disclosure to those skilled in the art. Like reference numerals refer to like elements throughout.

The terminology used herein is for the purpose of describing particular exemplary embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

FIG. 1 illustrates a multi-purpose modular wearable interface according to some embodiments of the present disclosure. Particularly, FIG. 1 shows an exemplary wearable interface device 10 that takes the form of a knee brace, with several regional enlargement views that selectively highlight various features of the exemplary device.

The exemplary wearable device 10 is designed to interface (e.g., press/fix/retain) a plurality groups of functional elements (such as skin contact pads 130) over a body part (e.g., a lower limb 140) of a user. The illustrated wearable device 10 comprises essentially a modular brace 110 that may be functionally separated into multiple sub-bracing units (e.g., brace members 110-1, 110-2, 110-3) and a plurality of external functional add-ons (e.g., add-on members 120-1, 120-2, and 120-3, collectively referred to as add-on members 120). In the illustrated embodiment, the modular brace 110 is a stand-alone piece of garment that is structurally separated from the functional elements (e.g., skin contact pads 130).

The modular brace 110 is provided with plurality groups of orienting slots 111 thereon, configured to maintain intra-group formation within one group of the skin contact pads 130. For instance, the regional enlarged view on the left hand side of FIG. 1 shows a total of six skin contact pads 130, which are arranged into two groups of three. Particularly, each group of three contact pads 130 is arranged in an up-right triangular formation, with one pad arranged over the top of the remaining two pads that are arranged laterally abreast each other.

Correspondingly, the regional enlargement view in FIG. 1 illustrates two groups of orienting slots 111 are provided on the modular brace 110, each group of slots being formatted into a pattern that substantially matches the designated formation (e.g., relative position) of the skin contact pads 130 (e.g., in this case, into a triangular pattern).

In the illustrated embodiment, the orientating slots 111 are distributed over the modular brace 110 with proper intra-group separations that takes into account the width of the skin contact pads, such that, in most applications, minimizes interference between neighboring pad units (e.g., avoid overlapping of the contact pads upon fastening of the brace member 110). Depending on application context, the intra-group pattern formation may be determined based on certain physiological features of the human anatomy. For instance, in the illustrated embodiment, the intra-group orientating slot pattern is correspondingly arranged to match the general layout of the quadriceps femoris muscle. However, it should be noted that, while the illustrated embodiment shows an application for the knee of a human user, the underline inventive concept of the instant disclosure may be applied to wearable devices for other parts of the body, e.g., the elbow, neck, or even torso.

Generally speaking, the relative position between certain groups of body features may remain substantially constant despite possible variance across different body sizes (e.g., groups of acupoint, tender points, trigger points, etc.). Accordingly, the design of the intra-group slot pattern may be at least partly determined by the designated body part on which the functional skin interface (e.g., pads 130) and the supporting brace unit (e.g., brace member 110) will be applied. For certain applications scenarios (e.g., point of care (POC) applications, where health care services are provided remotely/away from extensive supervision of medical professionals), the provision of the pre-arranged intra-group fixation mechanism may help to increase foolproof level for amateur/self-guided users, thereby ensuring ease-of-use while maintaining device application accuracy.

The exemplary modular brace 110 is further provided with adjustment mechanisms (e.g., width/length adjusters 112/114) configured to allow inter-group separation adjustment between groups of the skin contact pads 130 over the body part of the wearer. For instance, in the lateral direction, a width adjustment mechanism 112 is provided between the groups of skin contact pads 130 to enable lateral separation adjustability between certain groups of contact pads (inter-group separation adjustment) while maintaining relative positions between members of contact pads within a group (intra-group formation retention). The inter-group adjustment mechanism may allow the brace member 110 to fit a wider range of users of varying body sizes, thereby achieving the design trend of one-size-fits-all.

The plurality of external add-on members 120 is configured to detachably couple the groups of skin contact pads through the orienting slots 111 in the modular brace 110. In the illustrated embodiment, the modular brace 110 is provided as a piece of garment to be worn around a limb of a user. Accordingly, the modular brace 110 defines an inward surface (e.g., surface 410a labeled in FIG. 4) that comes in contact with the skin of a wearer, and an outward surface (e.g., surface 410b in FIG. 4) opposite to the inward surface. In some embodiments, the inward surface of the modular brace 110 is configured to press over the skin contact pad 130 without sticktion, thereby maintaining formation orientation among a same group of functional skin interfaces (e.g., pads 130) over body part of a wearer.

Depending on specific applications, the functional skin interface (e.g., pads 130) may take various forms. For instance, in some embodiments, the skin contact pads 130 may be provided in the form of active therapeutic devices, such as neuromuscular electrical stimulation (NMES) pads or micro-thermal therapy pads (which may comprise electrical based or infra-red based heating elements). In such applications, the external add-on members 120, which are designed to couple the skin contact pads through the orientating slots 111, may be provided with corresponding electrical components and onboard power sources to support the function of the therapeutic pads.

In some embodiments, the skin contact pads 130 may be provided in the form of trans-dermal therapeutic pad, such as a pain relief patch. In such applications, the external add-on member 120 may be provided with a drug reservoir that, upon coupling/engagement with the skin contact pads 130, facilitates delivery of therapeutic substances thereto, e.g., via capillary arrangement.

While some of the applications do not necessarily require accurate alignment among the skin contact interfaces, certain embodiments would be benefited from the intra-group orientation fixture arrangement. For example, in some embodiments, the functional skin contact interfaces may take the form of acupuncture patches. For such applications, accurate positioning and intra-pad orientation retention would be desired to ensure therapeutic efficacy, as well as to accommodate for inevitable body movements of the wearer.

In other applications that involves the capture of range of motion/motion tracking data for injury prevention or therapeutic purposes, the skin contact interfaces (e.g., pads 130) may take the form of precisely placed physiological sensor components. Such sensor devices may be configured to, upon coupling to the corresponding external add-on member 120, extract or otherwise obtain physiological information associated with a body part of a user (e.g., tracking of joint movement, joint range of motion, joint mobility, joint loading, joint angles, etc). In such embodiments, the intra-group orientation mechanism (e.g., the intra-group slots 111) incorporated by the exemplary brace member 110 would not only provide a fool-proof arrangement that guides users to achieve correct formation alignments among a group of functional contact interfaces, it also helps to retain position of the properly aligned pads over the body parts of a user throughout the duration of the dressing of the modular brace device.

In some embodiments, the general construction of the modular brace 110 comprises a pliant material (e.g., flexible fabric/cloth). In contrast, the general construction of the external add-on member 120 may comprise a substantially rigid material that is self-sustainable in shape and form, thereby forming a housing member that provides structural support and protective shielding for other functional devices that may be housed inside (e.g., sensor circuits, power unit, transceiver components, etc).

In some embodiments, the external add-on member 120 may incorporate structural support characteristics. For example, the rigid housing of the external add-on member 120 may be integrated with torsional spring that provides directional rigidity, so as to generate/enhance the physical support/load bearing capacity of the modular brace 110 along a predesigned direction/orientation. In some embodiments, the external add-on member 120 may incorporate elastic components configured to generate tensile or compression force upon coupling to the modular brace unit 110, thereby enhancing the load sharing capability of the brace device and facilitating strain relief for the brace wearer.

In some embodiments, the exemplary wearable device 10 is configured to serve as an interface between a wearer and an intelligent health promotion service system (IHPSS). The IHPSS may be a multimedia interaction system that utilizes the exemplary wearable device as a user interface to gather dynamic physiological data of a wearer, so as to enable remote data processing and real-time interactive feedback.

For instance, the wearable device 10 may be configured to interface plurality groups of skin-mounted sensor pads (e.g., pads 130) over a body part of a wearer. In such application, the wearable device 10 may comprise a modular brace 110 that includes modular bracing members 110-1, 110-2, 110-3, each being structurally separated from the sensor pads. The modular brace 110 is provided with plurality groups of orienting slots 111 distributed thereon, each being configured to maintain intra-group orientation within a group of sensor pads. Meanwhile, the modular brace 110 is configured to allow inter-group separation adjustment between the groups of the sensor pads over the body part of the wearer. The wearable device 10 further comprises a plurality of sensor modules 120-1, 120-2, 120-3, each being configured to be detachably coupled to corresponding groups of sensor pads through the orienting slots in the modular bracing member. One or more of the sensor modules 120 may be provided with physiological sensing circuits capable of establishing wireless communication with the multimedia interaction system.

In some embodiments, off-the-shelf components are utilized as the skin contact interface (e.g., pads 130). For example, in some embodiments, reusable pads such as neurostimulation electrodes from Axelgaard are adopted. The use of existing certified disposable components (e.g., the skin-mounted pads) may help to maximize device component accessibility and reduce manufacturing costs. In some embodiments, the inward surface of the modular brace 110 around the orientating slots 111 may be provided with non-sticky frictional texture configured to press over the back of the sensor pads without sticktion. While the incorporation of self-attaching components (e.g., stitching, adhesives, or a hook and loop arrangement, or other forms of direct surface to surface attachments) for retaining replaceable components (e.g., electrode pads 130) has been common place among wearable devices, such sticky material around the sensitive disposable components often degrades prematurely with continued usage and/or undesirably invite the accumulation of filth and dirt. Thus, such conventional arrangement may result in increased cleaning difficulty and hence reduce the product life of the wearable device. The intra-group orientation mechanism and the non-stichktion design of the instant disclosure may help to improve the reliability and longevity of the wearable device.

Figure 2A:
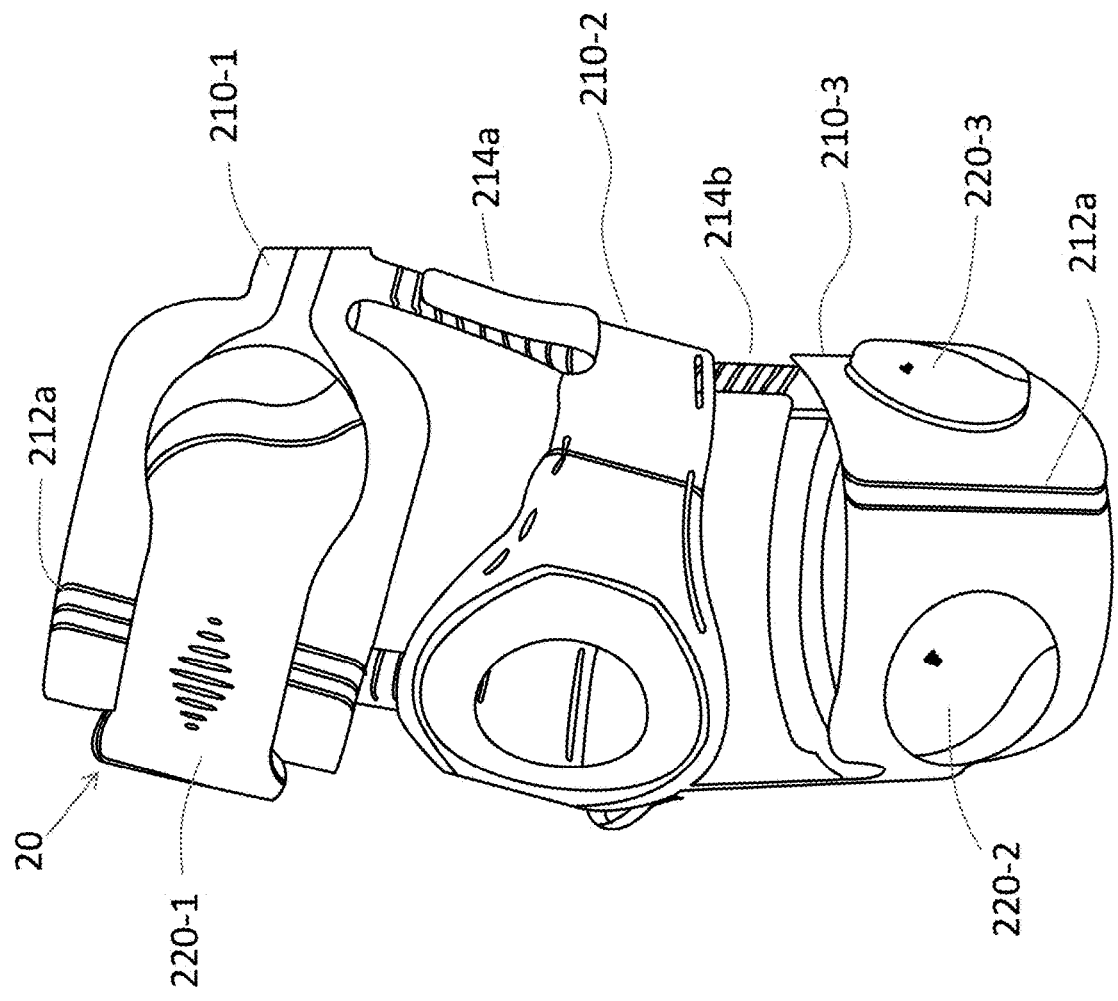

FIGS. 2A and 2B illustrate embodiments of wearable interface devices in accordance with some embodiments of the present disclosure from a frontal aspect view.

The exemplary modular brace member 20 (as well as brace 20') takes the form of a knee brace, and adopts a multi-sectional modular design. For instance, each of the modular braces 20 (or 20') comprises an upper bracing member 210-1 (or 210-1'), a mid bracing member 210-2 (or 210-2'), and a lower bracing member 210-3 (or 210-3'). As will be better visualized in the subsequent figures, each of the exemplary modular bracing members is capable of forming an annular wrap that allows each individual brace member to be self-retained over a body part of a wearer.

In some embodiments, the main portion of each structurally separated member (e.g., brace member 210-1, 210-2, etc) comprises a flexible garment or wrap. In some embodiments, the brace members are constructed with breathable material having high-compression and anti-slip characteristics. For instance, the elastic garment component of the modular brace may utilize synthetic fiber fabrics (including, e.g., anti-bacteria fabric, such as silver fiber fabric) with suitable surface treatments. The surface treatment may include water repelling coating treatment, surface friction modification, antimicrobial surface treatment, and anti-odor surface treatment. In some embodiments, the garment material and construction may be provided with pliant and non-slip characteristics, so as to constrain movement of the brace member over body parts of the wearer through friction and compression force, thereby minimizing undesirable rubbing, deice dislocation, or misalignment issues.

Compared with the pliant construction of the modular brace members, the external add-on member (e.g., members 220-1, 220-1', etc) is provided with an outer shield/housing unit that comprises substantially rigid material (e.g., capable of retaining its physical shape and form without substantial deformation absent the exertion of external force). In some embodiments, the exterior construction of the external add-on members may include a suitable combination of polymer material such as, e.g., ABS plastic, polyethylene, ultrahigh molecular weight polyethylene, polypropylene, polybutylene, urethane, neoprene and other natural and synthetic polymers. In some embodiments, the external add-on member may include metallic materials, e.g., stainless steel and spring steel. In some embodiments, the external add-on members may be formed by molding technique (as in, e.g., injection molding), by vacuum molding, by machining, by stamping, by electrochemical milling, by sputtering, by chemical vapor deposition, or by other applicable manufacturing methods.

In some embodiments, the external add-on member (e.g., members 220-1/220-1') may be constructed to traverse across more than one group of intra-group orientating slots and configured to couple more than one group of functional skin contact units (e.g., pads 130, which are not visible in the instant view).

In some embodiments, the external add-on member (e.g., members 220-2, 220-3) may be configured to cover a single group of orientating slots. It is noted that the coverage of an external add-on member need not be limited to the region within an individual modular brace member. For instance, in certain applications, an external add-on member may be configured to traverse across/over different modular brace members (e.g., from the upper brace member 210-1 through the middle brace member 210-2 to the lower brace member 210-3).

To form the complete modular brace 20/20', interconnecting members 214a/214b (or 214') are provided between the each pair of the neighboring members, so as to enable easy yet secure inter-modular coupling. For instance, as can be seen from the embodiments shown in FIGS. 2A and 2B, at least one of the upper brace member 210-1/210-1' and the lower bracing member 210-3/210-3' is provided with an interconnecting member 214a/214b/214' configured to engage the mid bracing member 210-2. In some embodiments, the interconnecting member (collectively referred to as interconnect 214) are made of pliant yet stretch-resistant material capable of retaining separation distance between groups of the functional skin interfaces (e.g., pads 130) in the vertical direction (with reference to the orientation shown in the illustrated figures). In some embodiments, the interconnecting member is provided with a length adjustment mechanism that enables adjustment of the separation distance along the vertical direction (will be illustrated in further detail in FIG. 5).

The self-retaining capability of each of the modular brace members allows them to be used individually as stand-alone units. The increased device modularity may therefore expand application flexibility. For instance, in some applications, the lower brace member 210-3/210-3' (and the corresponding external add-on member 220-3/220-3') may be individually applied as a knee support band that provides load relief capability around the patellar ligament of the wearer. On the other hand, for applications that call for more secure device retention or accurate device alignment (e.g., in applications that involves motion tracking under severe body motion/movement conditions), the lower brace member 210-3 may be applied in cooperation with the mid brace member 210-2. In such embodiments, the mid brace member 210-2 may serve as an anchoring garter over a joint of a wearer, thereby augmenting the lower brace member 210-3 for better maintaining of orientation reference for the onboard sensor device in the add-on members.

In some embodiments, such as that illustrated in FIG. 2A, the interconnecting member 214a and 214b are provided in the form of suspending straps. For instance, the strap may be an integrated extension on either one of the modular sub-brace member 210-1/210-2/210-3. Correspondingly, the adjacent member may be provided with a strap-receiving slot that allows the interconnect strap to be fastened therethrough. In some embodiments, the interconnecting member (e.g., member 214a/214b) may incorporate length adjusting mechanism (which, in the illustrated embodiment, takes the form of a hook and loop arrangement), so as to enable separation adjustment among different groups of orientating slots in the vertical direction (with reference to the orientation shown in the illustrated figure). For instance, the long and narrow strap configuration shown in FIG. 2A provides a wide range of continuous adjustability for fine-tuning the separation distance between groups of skin contact interfaces (e.g., pad 130). In other applications where wide range of adjustment is deemed unnecessary, relatively simple interconnecting mechanism may be adopted. For instance, as shown in the embodiment of FIG. 2B, a button/buckle style fastening mechanism (e.g., member 214') is provided between the upper brace member 210-1' and the mid brace member 210-2'. In such case, multiple buttons may be placed on the brace member at predetermined pitch intervals to enable adjustability.

Figure 3:
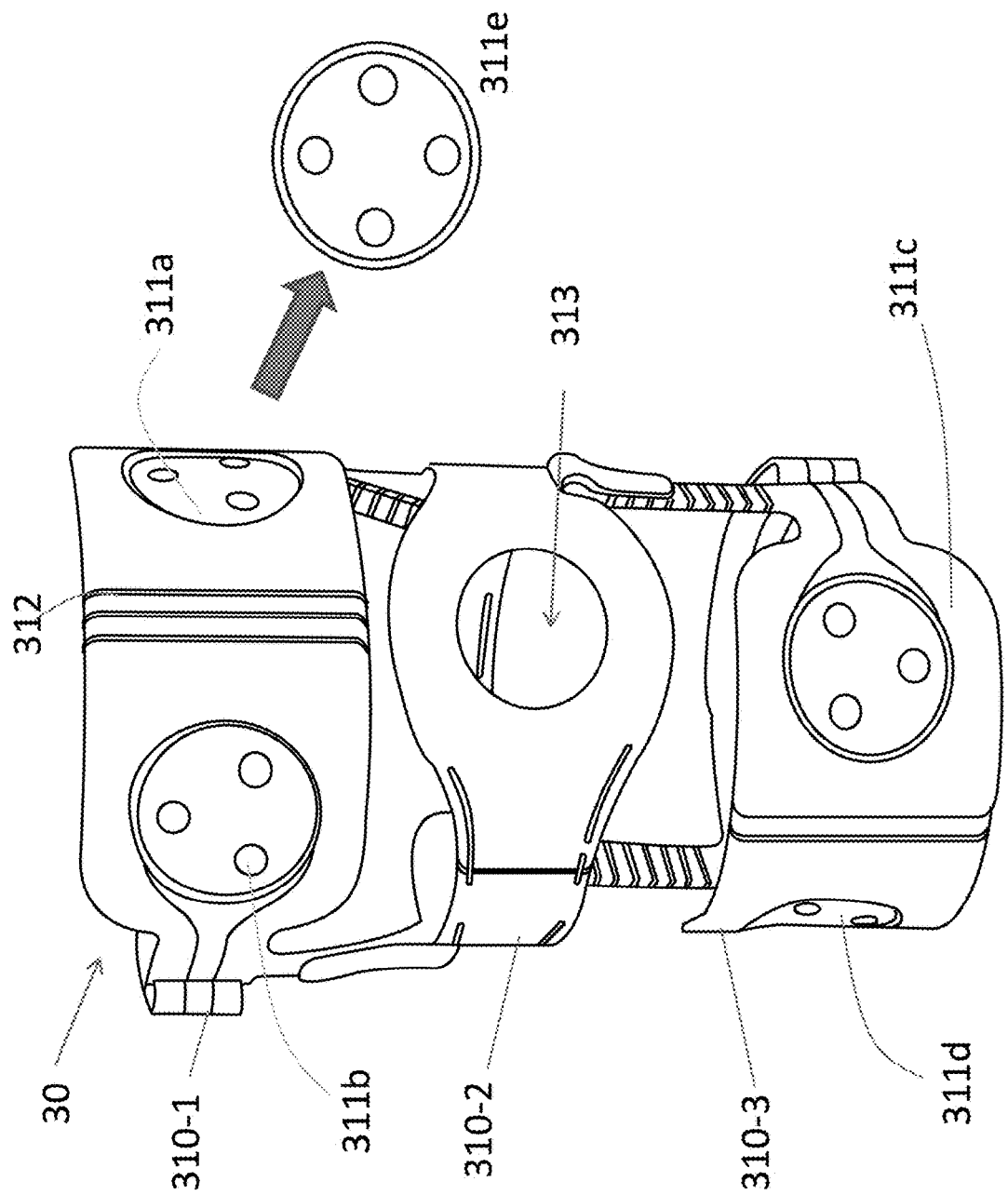
FIG. 3 illustrates frontal aspect view of an exemplary modular brace member of a wearable interface device in accordance with some embodiment of the instant disclosure.

FIG. 3 illustrates frontal aspect view of an exemplary modular brace member of a wearable interface device in accordance with some embodiment of the instant disclosure. Particularly, FIG. 3 shows a modular brace 30 with the external add-on members (e.g., members 120) removed, in accordance with some embodiments of the instant disclosure. This brace-only view provides a clearer visualization of the intra-group orientating slots (e.g., slot group 311a/311b/311c/311d).

In the illustrated embodiment, the upper brace member 310-1 carries two groups of orientating slots 311a and 311b, which are distributed substantially symmetrically on either side of the central strips 312. In addition, each group of the orientating slots 311a/311b comes with a number of three through holes arranged within a circular slot carrier. In some embodiments, the slot carriers may be an integral part of the pliant brace module. In some embodiments, the slot carrier may be a substantially rigid piece of disk-like structure with through-slots arranged thereon, configured to couple the modular brace member (e.g., member 310-1). In some embodiments, the slot carrier is designed as a replaceable unit provided with varying slot size, slot pitch, and/or slot number, so as to expand the application flexibility of the modular brace unit. For instance, in the illustrated embodiment, the three-slot pattern 311a on the exemplary upper brace member 310-1 may be changed into a four-slot pattern 311e upon replacement of a detachable slot carrier.

In some embodiments, the modular brace members (e.g., members 310-1, 310-2, and 310-3) may be provided with features that help increase ergonomic adaptability over a wearer's body. For instance, in some embodiments, the mid brace member 310-2 may be provided with a thinner, more pliant and flexible central region to cope with the pointy portion of a joint (e.g., olecranon of an elbow). In some embodiments, the brace members may be provided with apertures to provide further accommodation for wearers' particular body features. For example, in the illustrated embodiment, the mid brace member 310-2 is provided with a popliteal cutout 313 configured to accommodate the structure and movement in the vicinity of the patella of a wearer's knee. The enhanced ergonomic accommodation of the mid brace member 310-2 may further increase the retaining capability over a hinge joint of the wearer, thereby establishing better orientation reference for the upper and the lower bracing members 310-1, 310-3.

It is also noted that, not all the modular brace members ought to be outfitted with intra-group orientating slots (e.g., slot pattern 311a/b/c/d/e). For instance, in the illustrated embodiment, the designated function of the exemplary mid brace member 310-2 focuses more on providing anchoring reference over a hinge joint of a wearer (e.g., a human knee, which normally experiences a more intense level of movement), thus is provided without an orienting slot.

Figure 4:
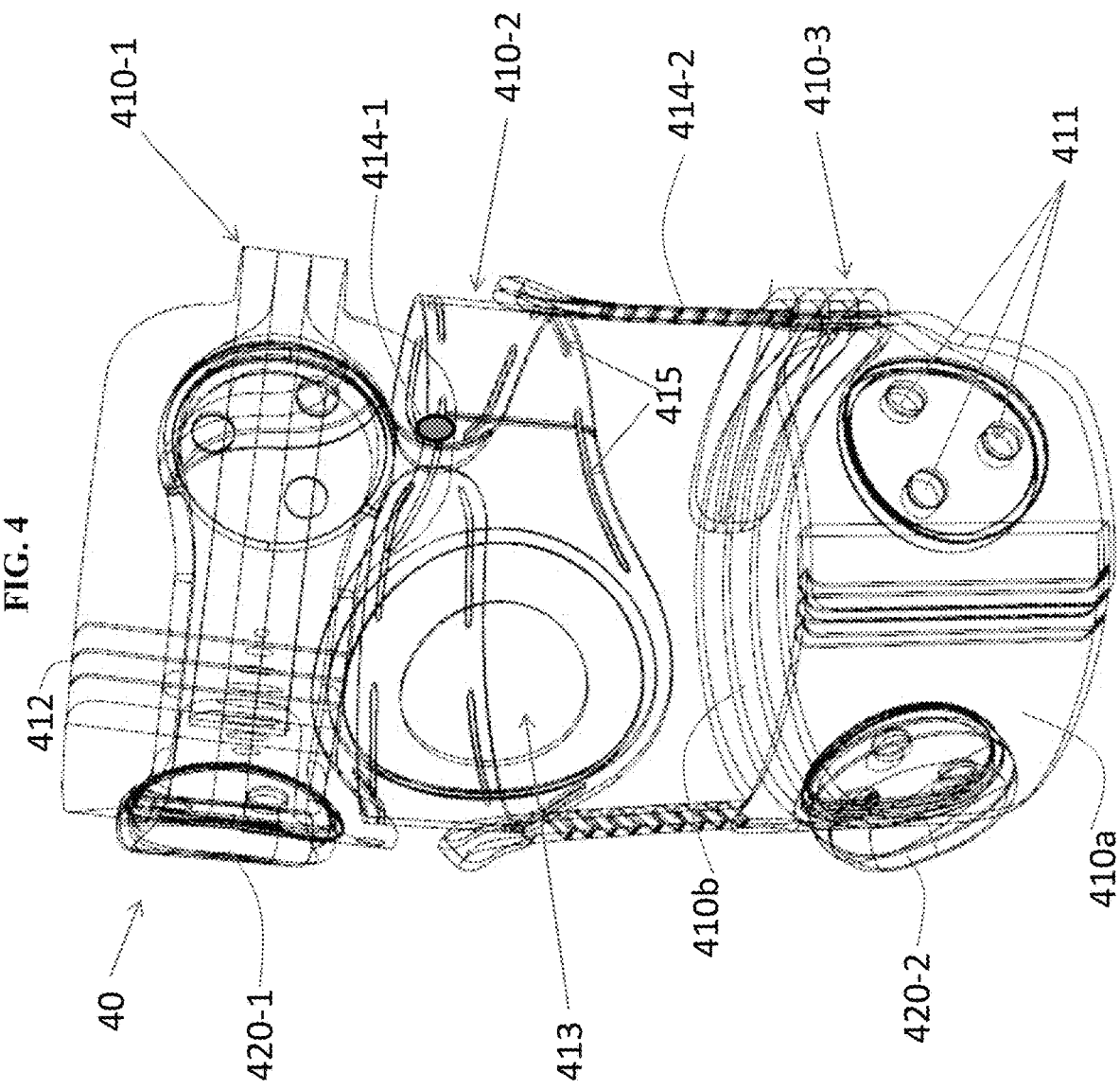
FIG. 4 illustrates a see-through view of an exemplary modular brace member of a wearable interface device in accordance with some embodiment of the instant disclosure.

FIG. 4 illustrates a see-through view of an exemplary modular brace member of a wearable interface device in accordance with some embodiment of the instant disclosure. Particularly, FIG. 4 shows a modular brace 40 with two of its external add-on members (e.g., members 420-1, 420-2)

installed, in accordance with some embodiments of the instant disclosure. This see-through view provides a clearer visualization of the interface region between the functional skin contact interfaces (e.g., pads 130) and the external add-on members (e.g., member 420).

In the illustrated embodiment, the exemplary upper brace member 410-1 is shown to be coupled with a multi-group type external add-on member 420-1. The exemplary multi-group type add-on member 420-1 is provided with an elongated profile that traverses laterally across two groups of orientating slots (which are arranged at the respective sides of the width adjustment mechanism 412). In some embodiments, the multi-group type external add-on member 420-1 may be replaced with a pair of single-group type add-on module, each of which covers a single group of orientating slots 411.

Similar to that shown in the previous embodiment, the mid brace member 410-2 is provided with a cutout hole 413 in the middle region thereof. A short buckle style engagement arrangement 414-1 is provided between the upper brace member 410-1 and the mid brace member 410-2, while a longer interconnect sling arrangement 414-2 is provided between the mid brace member 410-2 and the lower brace member 410-3. A plurality of interconnecting slots 415 are arranged at the upper and lower edge regions of the mid brace member 410-2, each being configured to engage an interconnecting member (e.g., sling member 414-2), so as to expend operational adjustability and increase adaptability for different practical applications.

The exemplary lower brace member 410-3 is shown with a single-group type external add-on member 420-2 installed over the group of orientating slots on the left hand side (with reference to the orientation as shown in FIG. 4). As shown in the instant illustration, the external add-on member 420-2 is coupled to the lower brace member 410-3 through physical contact over the outward surface 410$a$ of the brace member. In some embodiments, the external add-on member (e.g., member 420-2) may be configured to be retained over the outer surface of the brace member though structural engagement with the underlying functional skin interface (e.g., pad 130) without direct interconnection with the brace member itself. In some embodiments, the external add-on member may be provided with bumps/protrusions that are configured to respectively extend into the corresponding orientating slots (e.g., slots 411) on the brace member, so as to provide enhanced retaining capability.

FIGS. 5A and 5B illustrate exemplary modular brace members in an unwrapped configuration in accordance with some embodiments of the instant disclosure. The unwrapped layout views of FIGS. 5A and 5B provides a clearer illustration on the exemplary construction of a modular brace device in accordance with the instant disclosure.

Each modular member 510-1/510-2/510-3 of the exemplary wearable device 50 is constructed with an elongated pliant strap body, each defining a longitudinal axis L (as explicitly labeled in FIG. 5B). The exemplary pliant strap body is provided with a pair of fasteners 516$a/b$, 516$c/d$ arranged at the respective end portions 510E1/E2 along the longitudinal axis. The fasteners (e.g., 516$a/b$, 516$c/d$) are configured to engage each other to form a loop, so as to allow the brace members to wrap around a limb of a wearer in a self-retaining manner. A pad retaining section (e.g., mid section 510C) is arranged between the fasteners at the central portion of the pliant strap body, over which separate groups of orientating slots (e.g., slot carrier 511) are distributed.

The pad retaining section 510C, which is provided with a greater strap width than the end portions 510E1, 510E2 (e.g., the width w in the direction normal to the axis L) of the brace member, may be provided with an adjustment mechanism 512 along the longitudinal axis direction between the separate groups of the orientating slots. The adjustment mechanism 512 is configured to enable inter-group distance adjustment between groups of the corresponding skin contact pads along the longitudinal axis direction. Exemplary width adjustment mechanism will be illustrated in further detail with respect to FIG. 6 below. In some applications, the strap width w of individual modular brace member (e.g., brace member 510-1/510-2, etc) is configured to remain within a certain width threshold, so as to prevent excessive hindrance to the movement of a wearer upon fastening of the wearable device.

In some embodiments, at least one of the upper brace member 510-1 and the lower bracing member 510-3 is provided with an interconnecting member (e.g., buckle 514 or sling 154') configured to engage the mid brace member 510-2. The interconnecting member may be designed to retain separation distance between groups of the skin contact pads (e.g., pads 130) in a direction normal to the longitudinal axis L. In some embodiments, the interconnecting member (e.g., the sling member 514'/514") is provided with a length adjustment mechanism that enables adjustment of the separation distance.

Referring to FIG. 5B, in the illustrated embodiment, the width adjustment mechanism 512 of the upper bracing member 510-1 is configured to be substantially in alignment with the cutout hole of the mid bracing member upon engagement with the mid bracing member (upon interconnection of the upper and the mid members). In contrast, the width adjustment mechanism 512' of the lower bracing member 510-3 is configured to substantially offset the cutout hole 513 of the mid bracing member 510-2 upon engagement there-with.

In some embodiments, at least one of the width adjustment mechanisms (e.g., member 512/512') and the length adjustment mechanisms (e.g., member 514/514'/514") is provided with visual positioning marks (e.g., scale marks provided on the interconnecting sling member 514") arranged between the separate groups of orientating slots, so as to provide convenient reference for users during occasions when prolonged removal of the wearable device is required (e.g., cleaning, drying).

Figure 6:
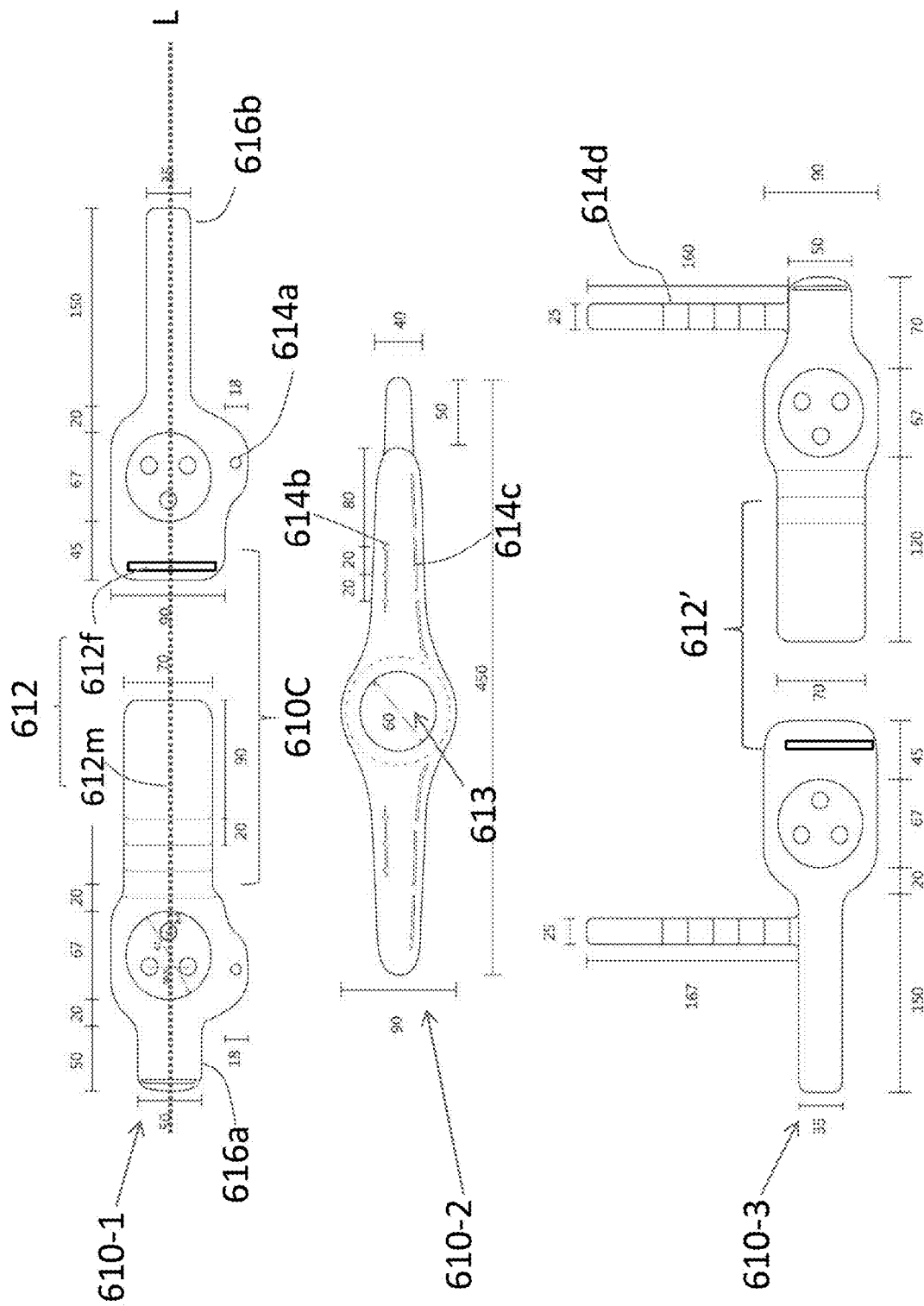
FIG. 6 illustrates unwrapped components of an exemplary modular brace member in accordance with some embodiments of the instant disclosure.

FIG. 6 illustrates unwrapped components of an exemplary modular brace member in accordance with some embodiments of the instant disclosure. While other comparable features (e.g., interconnecting members 614$a/b/c/d$, brace end couplers 616$a/b$, etc) of the exemplary modular members 610-1/610-2/610-3 are omitted from further discussion for the sake of the brevity of disclosure, FIG. 6 provides a clearer view of one exemplary arrangement of a width adjustment mechanism 612/612'.

In some embodiments, the lateral inter-group separation adjustability in the modular brace member (e.g., member 610-1/610-3) may be achieve by a two-piece adjustable arrangement 612/612'. For instance, in the illustrated embodiment, each of the upper and the lower brace members 610-1 and 610-3 is of a two-piece construction. Particularly, the central region 610C of the exemplary upper brace member 610-1 includes a male adaptor portion 612$m$ and a female adaptor portion 612$f$, which are configured to engage each other while providing a range of width adjustability. In the instant illustration, exemplary dimensions of various device features are provided (in millimeter) for referencing purpose. It should be noted that the actual feature sizes should depend on specific operational needs or particular application requirements.

Figure 7:
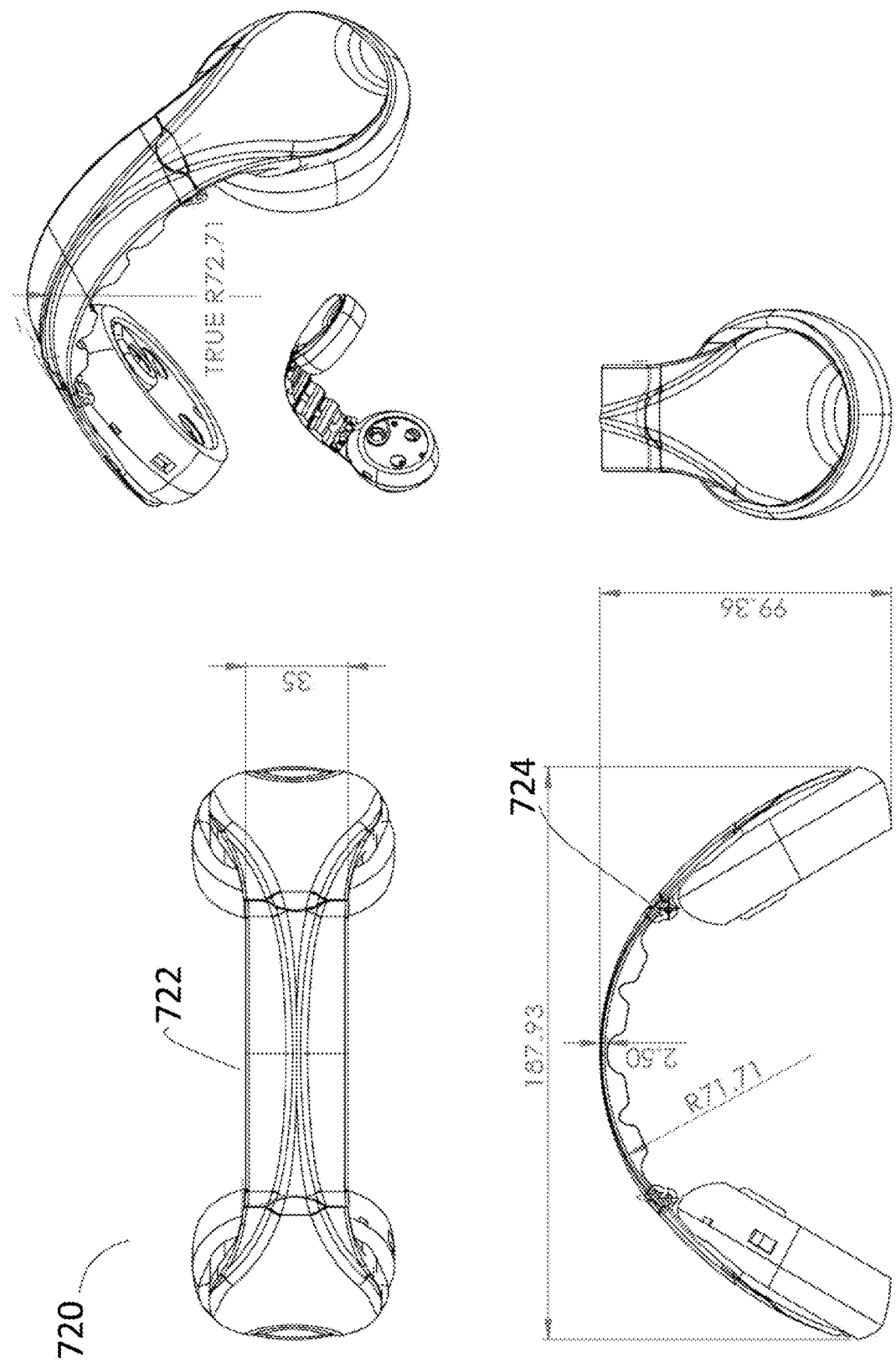
FIG. 7 illustrates an exemplary housing structure of an external add-on member in accordance with some embodiments of the instant disclosure from various points of view.

FIG. 7 illustrates an exemplary housing structure of an external add-on member in accordance with some embodiments of the instant disclosure from various points of view.

The illustrated external add-on member 720 presents an exemplary arrangement of a multi-group type external add-on member. The multi-group type add-on member 720-1 is provided with an elongated profile designed to traverse across two groups of orientating slots (e.g., slots 111 as shown in FIG. 1). In some embodiments, width adjustment mechanism may be incorporated in the middle cross-member 722 (e.g., telescopic structure). In some embodiments, hinge mechanism (e.g., hinge 724) may be provided on the substantially rigid external add-on member to enhance its conformity over the modular brace member. In some embodiments where electronic equipment is housed within, visual indications (e.g., lights or display) may be provided on the external add-on member to enable quick and convenient reference to the operating status of the embedded functional devices. For instance, in some embodiments, the external add-on member is provided with an observable light unit that provides indication to the battery status of the electronic devices housed therein. In some embodiments, light indicators are provided on the external add-on member to signal proper connection between the add-on member and the corresponding functional skin interface (e.g., pads 130 as shown in FIG. 1).

Figure 8:
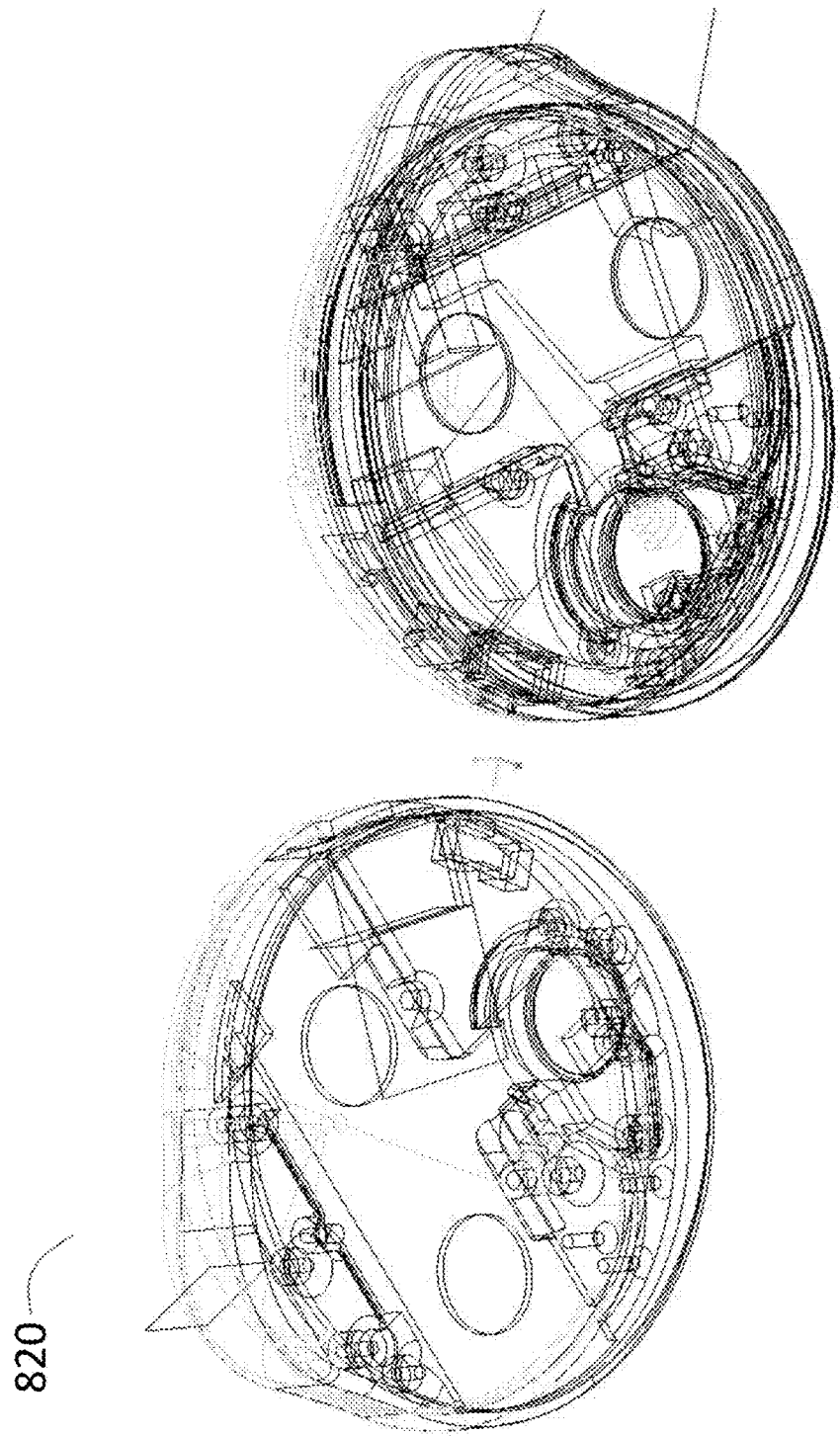
FIG. 8 illustrates partial see-through diagram of exemplary external add-on members in accordance with some embodiments of the instant disclosure.

FIG. 8 illustrates partial see-through diagram of exemplary external add-on members in accordance with some embodiments of the instant disclosure.

The illustrated external add-on member 820 presents an exemplary arrangement of a single-group type external add-on member, whose shape and dimension are configured to cover a single group of functional skin interfaces (e.g., pads 130). Similar to the previous embodiment, in some embodiments, visual indications (e.g., lights or display) may be provided on the external add-on member 820 to enable quick and convenient reference to the operating status of the embedded functional devices. For instance, in some embodiments, the external add-on member is provided with an observable light unit that provides indication to the battery status of the electronic devices housed therein. In some embodiments, light indicators are provided on the external add-on member to signal proper connection between the add-on member and the corresponding functional skin interface.

In some embodiments where the gathering of precision physiological information is desired, the external add-on members may be provided with a variety of physiological sensor devices to meet the needs. For example, one or more of the external add-on members (e.g., member 120) may be provided with micro-electronic components that selectively incorporate the functionality of, e.g., accelerometer, gyrometer, motion sensor, proximity sensor, optical sensor, magnetometer, pressure/force sensor, hydration sensor, position sensor, position tracking sensor (e.g., global positioning sensor (GPS)), etc. The sensors may include one or more of optical-based sensors, magnetic sensors, inductive sensors, capacitive sensors, electric current sensors, resistive sensors, magneto-resistive sensors, infrared sensors, inclinometer sensors, piezoelectric materials or piezoelectric-based sensors, blood-oxygen sensors, heart-rate sensors, laser or ultrasound based sensors, and electromyography type sensors.

In some embodiments, the physiological sensor components may be configured to measure the position, movement, and/or acceleration of the external add-on member over the modular wearable device (e.g., modular brace 110) in different orientation references (e.g., x, y, and/or z-axis). In some embodiments, the physiological sensors may incorporate micro solid-state or micro-electromechanical systems (MEMS) devices. In some embodiments, the physiological sensors may be configured to measure/sense position and orientation, acceleration, velocity, vibration or shock along a single, or multiple axes. For instance, in some embodiments, the micro sensor devices may include an integrated 3-axis gyroscope, 3-axis geomagnetic sensor, and 3-axis accelerometer capable of measuring an absolute orientation vector in form of Quaternion or Euler angles.

Figure 9:
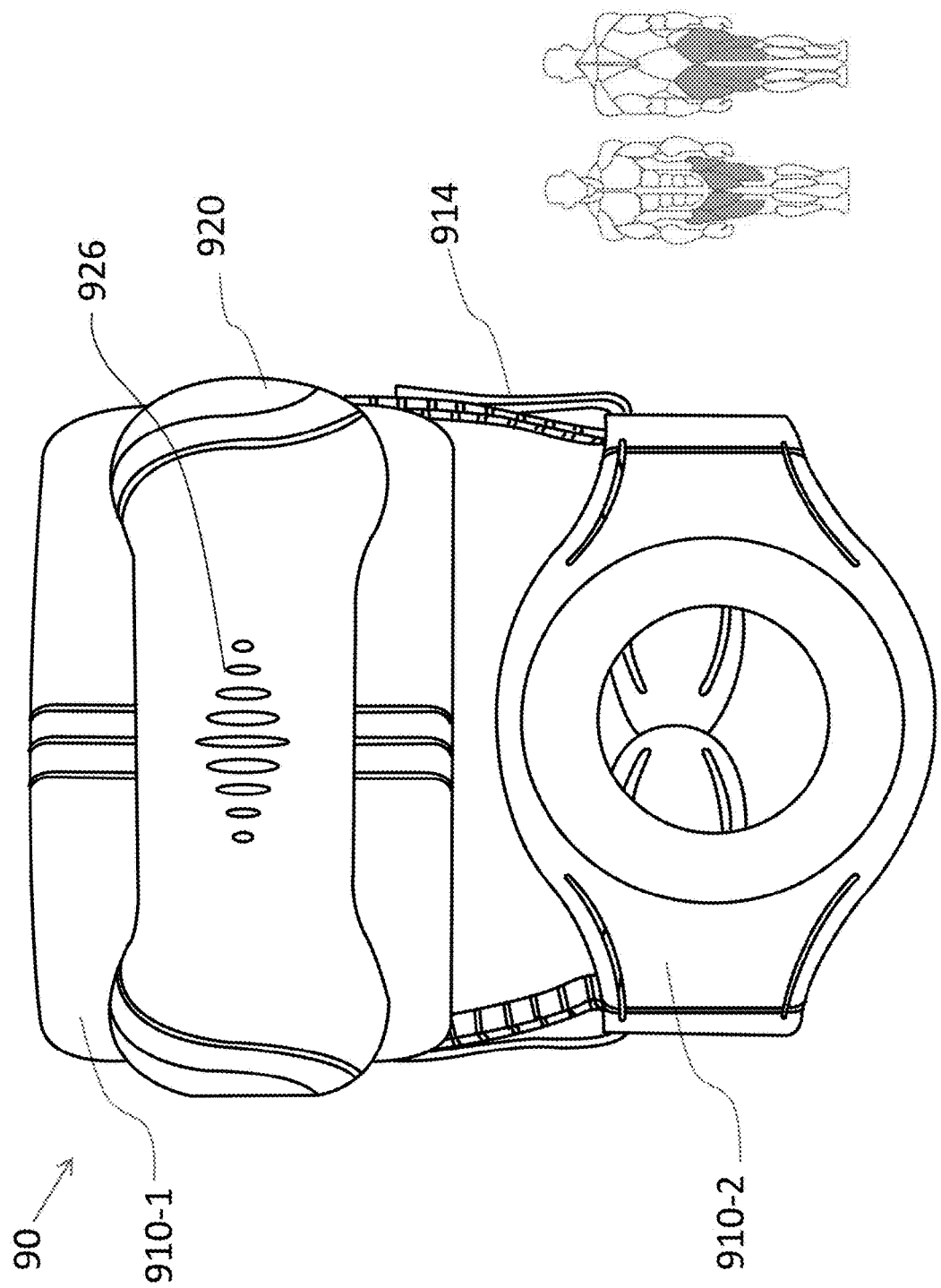
FIG. 9 illustrates an application configuration of a modular brace member, according to some embodiments of the instant disclosure.

FIG. 9 illustrates different application configurations of a modular brace member, according to some embodiments of the instant disclosure.

The modularity in the exemplary brace member in accordance with the instant disclosure allows the wearable interface device to be utilized with greater degrees of flexibility. For instance, as shown in FIG. 9, in certain applications, only the upper and the mid brace modules 910-1 and 910-2 are utilized (which are interconnected through the sling member 914). In such configuration, only one external add-on member 920 (on which an indicating light unit 926 is provided) is adopted to monitor the physiological activity of a wearer's quadriceps femoris muscle. Meanwhile, the mid brace member 910-2 provides additional anchoring capability for the modular brace system, which further aids the retention accuracy of the corresponding sensor devices.

Likewise, in some applications, the modularity of the exemplary wearable interface system allows the adoption of only the mid and the lower brace members (e.g., members 110-2 and 110-3). In such configuration, physiological signals associated with plantar flexion and dorsiflexion activities of the wearer may be detected and recorded. The selective omission of certain brace components may help reducing burden to a user in certain occasions, and help pin-pointing therapeutic efforts to particular region of a user's body.

Figure 10:
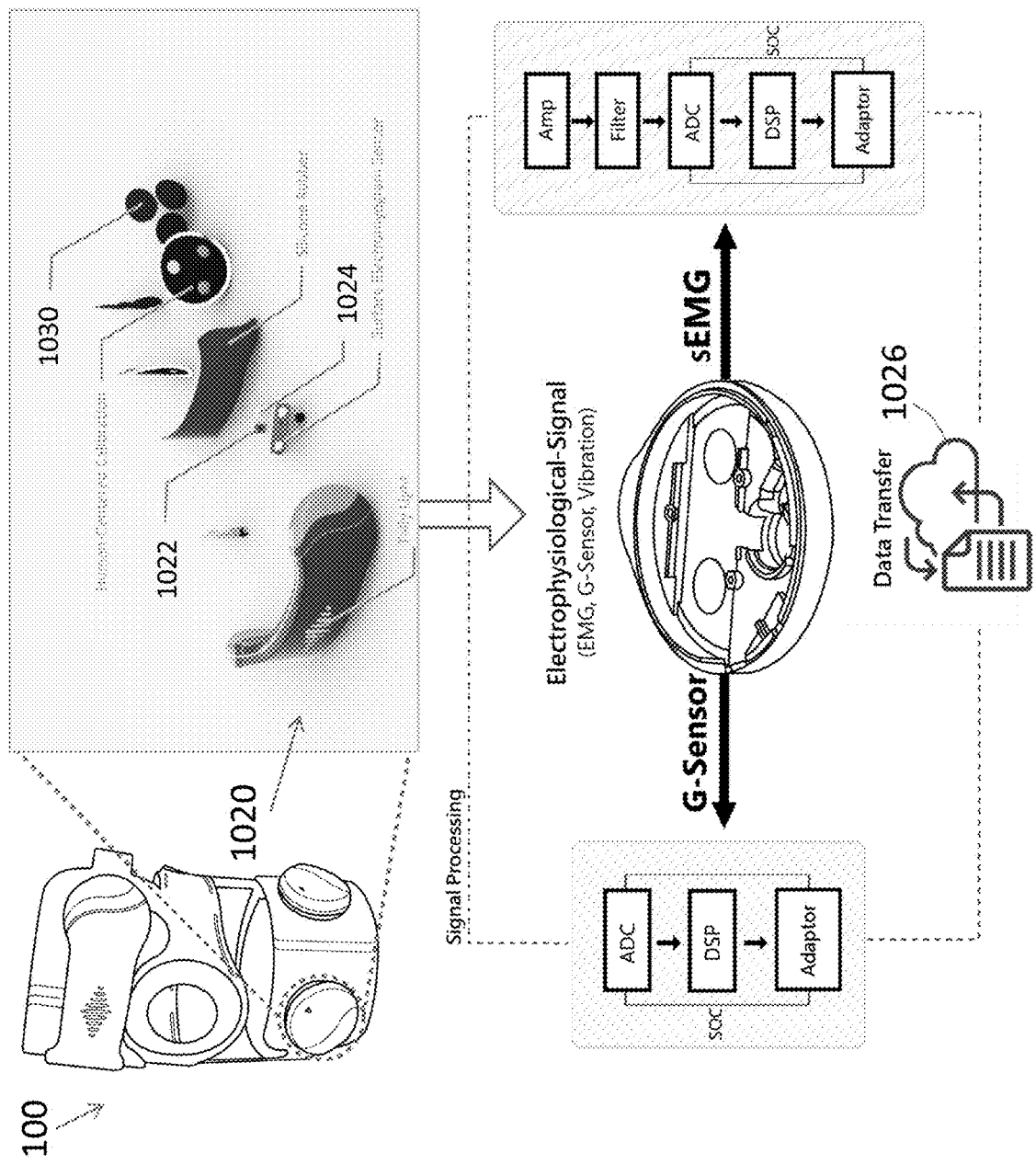
FIG. 10 illustrates a component block diagram of an exemplary external add-on member for a wearable interface device in accordance with some embodiments of the instant disclosure.

FIG. 10 illustrates a component block diagram of an exemplary external add-on member for a wearable interface device in accordance with some embodiments of the instant disclosure. Particularly, FIG. 10 illustrates an exemplary signal processing flow between components of a wearable interface device 100 in accordance with some embodiments of the instant disclosure.

In some embodiments, the hardware components of the exemplary add-on module 1020 may include: electrode patch or myoelectric sensing elements (e.g., pads 1030), orientation sensing elements (e.g., nine-axis inertial sensor 1022), power source (e.g., battery 1024), and associated controller circuits (not particularly shown). The data received through the myoelectric measurement module (e.g., add-on module 1020) may be transmitted to a host system through associated data transceiving mechanisms (e.g., communication circuitries, such as wireless transceiver 1026). The collected information from the wearable interface device 100 may thus be provided to a computing system in a dynamic, real-time fashion.

Myoelectric signal measurement refers to attaching electrodes to the surface skin of the muscle to measure the voltage change of the muscle during activity. Generally, the larger the EMG signal, the more motor units involved in the activity of the muscles, and therefore the higher the degree of excitement of the motor units, so the EMG may be used to infer the degree of local muscle activity. Using the above arrangement, the surface electrode pads 1030 can extract the myoelectric signals of various muscle groups, and after the signal is measured through the sensing unit, the signal may be amplified and processed before being sent to a host device for real-time screen display. Meanwhile, relevant information may be stored in the host device. In addition, the relevant information from the signal obtained by the nine-axis inertial sensing components may be directly stored in the host device, and be processed by backend system for data analysis and evaluation.

In some embodiments, the host device may be an intelligent health promotion service system, e.g., an interactive multimedia system designed for lower limb muscle rehabilitation. In some embodiments, the target training muscle groups of the service system may include quadriceps femoris, knee joint muscles, gluteal muscles, tibial anterior muscles, gastrocnemius muscles, and soleus muscles. According to the research of the rehabilitation physicians from the National Cheng-Kung University Hospital, the muscle strengthening required for complete lower limb rehabilitation include quadriceps, tibial anterior, gastrocnemius, soleus and other four major muscle groups, which can be divided into three major movements: knee extension, dorsiflexion, and plantar flexion. The training of the four major muscle groups of the lower limbs may effectively improve the muscle endurance of the lower limbs.

Figure 11:
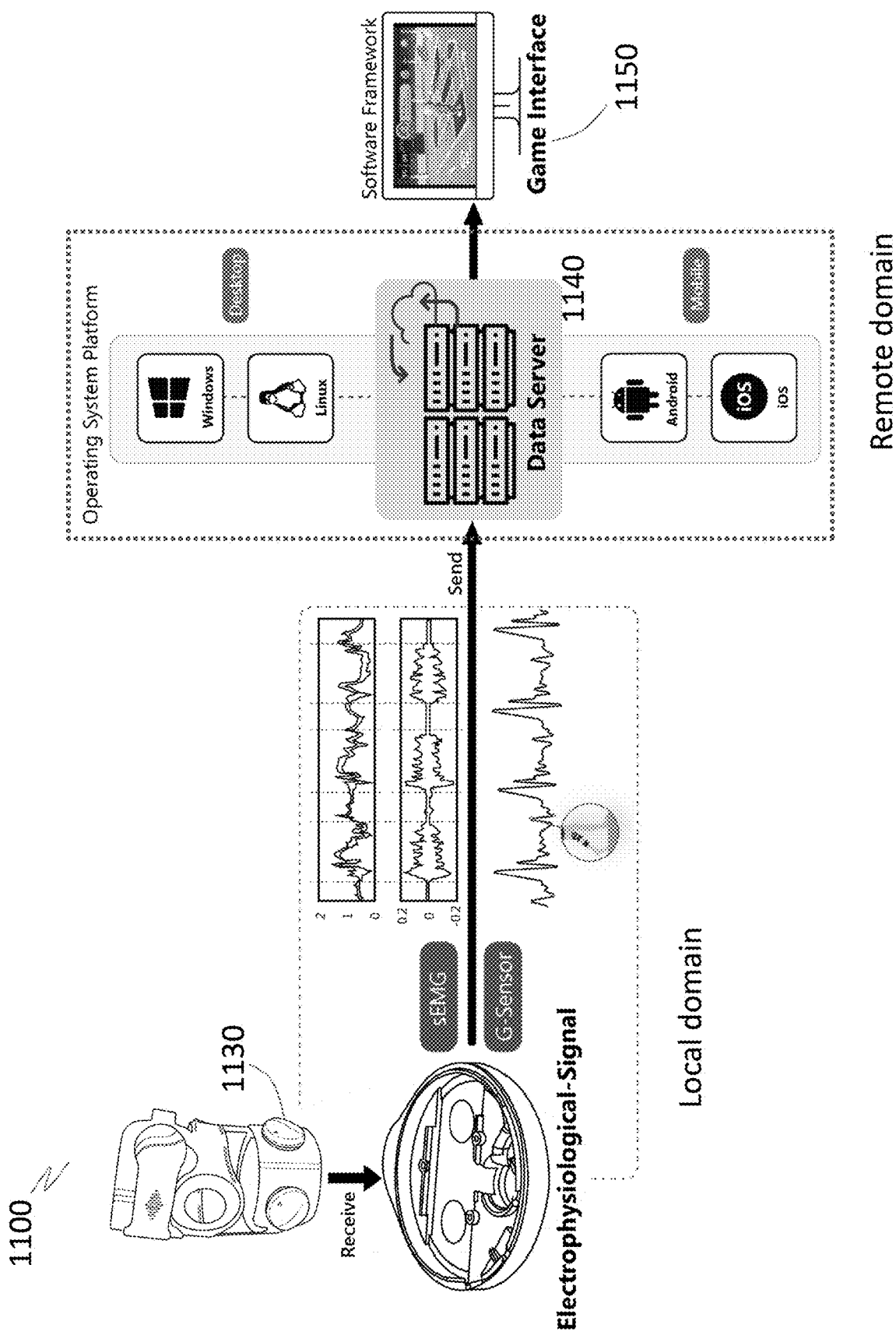
FIG. 11 illustrates a schematic signal processing flow for an intelligent health promotion service system (IHPSS) that utilizes a wearable interface device in accordance with some embodiments of the present disclosure.

FIG. 11 illustrates a dynamic signal processing flow for an exemplary intelligent health promotion service system (IHPSS) that utilizes a wearable interface device in accordance with some embodiments of the present disclosure.

The exemplary system 1100 may comprise components reside in a local domain (e.g., point-of-care location, such as a patient's home premises), and components that are maintained in a remote location (e.g., remove server in a medical facility or health service provider). For instance, a wearable interface device that incorporates a sensor pad 1130 may be provided locally within a patient's reach. Likewise, the multimedia system 1100 may include a user interaction interface (e.g., display device 1150). On the other hand, a host device 1140 (e.g., a backend server) may be maintained remotely at a centralized location.

In the illustrated embodiment, the exemplary service system 1100 is designed to generate dynamic audio-visual contents that are integrated into an interactive game format, based on a user's captured motion data and other physiological information (e.g., rehabilitation actions). For instance, in some embodiments, the multimedia content is manifested in a map-style stage/level-up challenge, which is designed to lead the users (e.g. patients) through interactive adventurous virtual games, thereby reducing the fatigue of the user's training experience and agitating self-training motivation.

In some embodiments, the interactive somatosensory system utilizes Unity 3D cross-platform software for project development, and use ICT software and hardware integration technology to develop an API package at the bottom of JAVA to connect the hardware. In some embodiments, the operations of the exemplary intelligent health promotion service system may be divided into five major processes, namely, 1) user basic data establishment, 2) customized parameter settings, 3) gamification rehabilitation experience, 4) user feedback, and 5) smart evaluation and recording.

Figure 12:
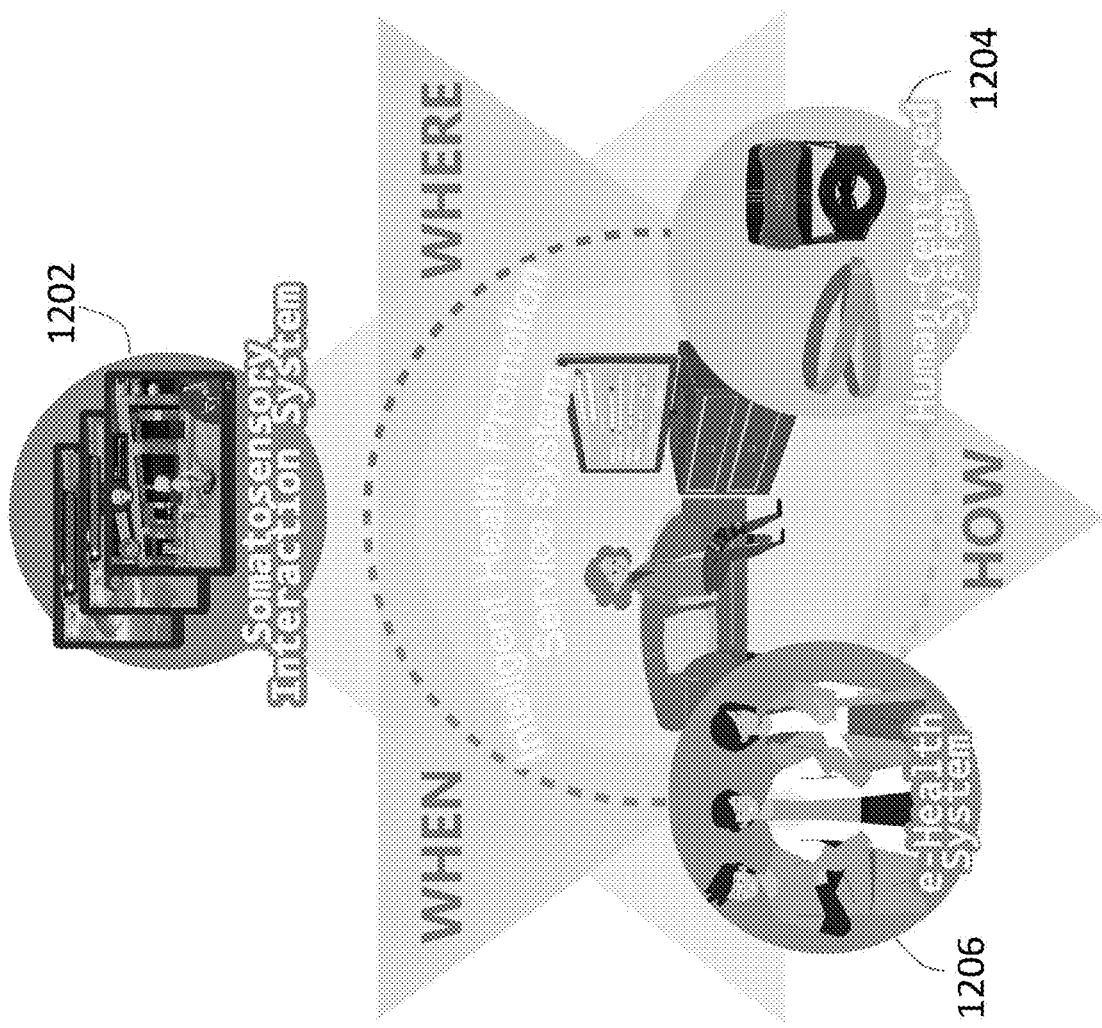
FIG. 12 illustrates a schematic architecture of an intelligent e-health promotion service system in accordance with some embodiments of the instant disclosure.

FIG. 12 illustrates a schematic architecture of an intelligent e-health promotion service system (IHPSS) in accordance with some embodiments of the instant disclosure.

For one thing, the exemplary smart health promotion service system 1100 is configured to facilitate integration of professional rehabilitation treatments, and provides a remote and digital service system for the elderly with frailty during the golden treatment period or the health promotion period. By way of example, an exemplary service system may be capable of accurately providing suitable rehabilitation program at a local domain (e.g., at a patient's home), so as to achieve three major service goals of "gamification, customization, and intelligence." In some embodiments, the smart health promotion service system is configured to provide nostalgic games to trigger resonance among the elderly, thereby increasing rehabilitation motivation.

In some embodiments, the system is configured to detect the condition of each muscle group of a user during training. The exemplary system may employ a wearable interface system (e.g., shown as the "smart human-centered system 1204" in FIG. 12) in accordance with the instant disclosure, which uses gait analysis to accurately divide the gait cycle technique, to assess the frailty level of the rehabilitator. The exemplary system can then facilitate the generation (or automatically establish) of a customized game rehabilitation treatment according to the needs of the rehabilitator, thereby building a high-quality clinical evaluation system. In addition, through deep learning and data analysis, the system may assist professionals to generate accurate rehabilitation plans for patients, and at the same time transmit the training status to their families, so that the patients can perform rehabilitation at the comfort of their home.

For another, this instant intelligent health promotion service system constitutes a new multimedia cloud-based system that integrates "interactive somatosensory system 1202," "smart human-centered system 1204," and "e-health system 1206" in a coherent and accessible service package. In some embodiments, the gamified rehabilitation content of the interactive somatosensory system 1202 may be provided with a retro nostalgic game style, so as to trigger resonance among the elderly users, thereby raising the fun level for the rehabilitator in the rehabilitation process; the interactive somatosensory rehabilitation content may be designed based on common clinical lower limb rehabilitation training actions, which may incorporate knee extension, dorsiflexion, plantar flexion, and other training actions. Through the virtual coaching style of the game presentation, the rehabilitation training may help guiding a patient through a rehabilitation training course that helps to spark motivation for continued rehabilitation. In other applications, the multimedia content of the service system may be tweaked to suit the particular flavor of the targeted user group. For example, in some embodiments where younger users are targeted, more visually exciting and physically demanding content may be delivered (e.g., athlete training programs).

Moreover, the human-oriented design spirit of this intelligent human-based system triggers the conception of a wearable rehabilitation aid (e.g., wearable interface 1204) designed for rehabilitators with customized scale adjustment and record design. In some embodiments, the wearable device incorporates a comfortable and easy-to-wear product design, and is capable of effectively recording the value, direction, and speed of a rehabilitator's muscle movement.

In some embodiments, through the employment of long and short-term memory (LSTM) algorithm of artificial intelligence deep learning and reinforcement learning (RL), the progression of muscle endurance of the rehabilitator may be evaluated. For instance, the collected data may be forwarded to the e-health system 1206 for analysis and fed to the associated professional personnel for evaluation and rehabilitation treatment reference, thereby enabling the prescription of a customized rehabilitation treatment course through the instant medical sharing system. Based on the rehabilitation needs of the rehabilitator, suitable rehabilitation treatment courses may be created, thereby shaping an interactive platform for the medical sharing system, in which family members of the rehabilitator may be informed of the patient's daily rehabilitation status, and where physicians may also use professional reports to continue interaction with patients and family members to further increase rehabilitation motivation and enhance rehabilitation effects.

Accordingly, one aspect of the instant disclosure provides a wearable apparatus for retaining plurality groups of skin contact pads over a body part of a wearer, comprising: a modular brace structurally separated from the skin contact pads, the modular brace is provided with plurality groups of orienting slots arranged thereon configured to maintain intra-group formation within one group of the skin contact pads, and is configured to enable inter-group distance adjustment between groups of the skin contact pads over the body part of the wearer; and a plurality of external add-on members configured to detachably couple the groups of skin contact pads through the orienting slots in the modular brace.

In some embodiments, the modular brace defines an inward surface and an outward surface; the inward surface of the modular brace is configured to press over the skin contact pad without sticktion to maintain positioning orientation thereof over body part of a wearer.

In some embodiments, the modular brace comprises an upper bracing member, a mid bracing member, and a lower bracing member; the bracing members are engage-able yet structurally detachable from one another; wherein each of the bracing members is self-retainable over a body part of a wearer.

In some embodiments, the mid bracing member is provided with a cutout hole for retaining over a hinge joint of the wearer to establish orientation reference for the upper and the lower bracing members.

In some embodiments, the mid bracing member is provided without an orienting slot.

In some embodiments, at least one of the upper bracing member and the lower bracing member includes a pliant strap body defining a longitudinal axis; the pliant strap body is provided with a pair of fasteners arranged at the respective end portions along the longitudinal axis, configured to engage each other to form a loop in the bracing member that wraps around a limb of the wearer, and a pad retaining section arranged between the fasteners having separate groups of the orientating slots distributed thereon.

In some embodiments, the pad retaining section is provided with a width adjustment mechanism along the longitudinal axis direction between the separate groups of the orientating slots, configured to enable inter-group distance adjustment between groups of the corresponding skin contact pads along the longitudinal axis direction.

In some embodiments, the width adjustment mechanism of the upper bracing member is substantially in alignment with the cutout hole of the mid bracing member upon engagement with the mid bracing member.

In some embodiments, the width adjustment mechanism of the lower bracing member substantially offsets the cutout hole of the cutout hole of the mid bracing member upon engagement with the mid bracing member.

In some embodiments, at least one of the upper bracing member and the lower bracing member includes an interconnecting member configured to engage the mid bracing member, thereby retaining separation distance between groups of the skin contact pads in a direction normal to the longitudinal axis.

In some embodiments, the interconnecting member is provided with a length adjustment mechanism that enables adjustment of the separation distance.

In some embodiments, at least one of the width adjustment mechanism and the length adjustment mechanism is provided with visual positioning marks arranged between the separate groups of orientating slots.

In some embodiments, each of the bracing members of the modular brace comprises elastic fabric material.

In some embodiments, each of the external add-on members comprises a rigid housing that provides structural retention.

In some embodiments, one or more of the external add-on member comprises physiological sensors in the rigid hollow housing.

Accordingly, another aspect of the instant disclosure provides a wearable apparatus for an intelligent health promotion service system, configured to interface a plurality groups of skin-mounted sensor pads over a body part of a wearer, comprising: a modular brace structurally separated from the sensor pads, the modular brace is provided with a plurality groups of orienting slots arranged thereon configured to maintain intra-group orientation between the sensor pads, and is configured to allow inter-group distance adjustment between the groups of the sensor pads over the body part of the wearer; and a plurality of sensor modules configured to be detachably coupled to the groups of sensor pads through the orienting slots in the modular bracing member; the sensor modules comprise physiological sensing circuits wirelessly communicative with the multimedia interaction system.

In some embodiments, the modular brace defines an inward surface and an outward surface; the inward surface of the modular brace is configured to press over the sensor pad without sticktion to maintain positioning orientation thereof over body part of a wearer.

In some embodiments, the modular brace comprises an upper bracing member, a mid bracing member, and a lower member; the bracing members are engage-able yet structurally detachable from one another; wherein each of the bracing members is self-retainable over a body part of a wearer.

In some embodiments, the mid bracing member is provided with a cutout hole for retaining over a hinge joint of the wearer to establish orientation reference for the upper and the lower bracing members, wherein the mid bracing member is provided without orienting slot.

In some embodiments, at least one of the upper bracing member and the lower bracing member includes a pliant strap body defining a longitudinal axis, the pliant strap body having: a pair of fasteners arranged at the respective end portions along the longitudinal axis, configured to engage each other to form a loop in the bracing member that wraps around a limb of the wearer, and a pad retaining section arranged between the fasteners having separate groups of the orientating slots distributed thereon; wherein the pad retaining section is provided with a width adjustment mechanism along the longitudinal axis direction between the separate groups of the orientating slots, configured to enable inter-group distance adjustment between groups of the corresponding sensor pads along the longitudinal axis direction.

In some embodiments, at least one of the upper bracing member and the lower bracing member includes an interconnecting member configured to engage the mid bracing member, thereby retaining separation distance between groups of the sensor pads in a direction normal to the longitudinal axis; wherein the interconnecting member is provided with a length adjustment mechanism that enables adjustment of the separation distance.

In some embodiments, at least one of the width adjustment mechanism and the length adjustment mechanism is provided with visual positioning marks arranged between the separate groups of orientating slots.

In some embodiments, the width adjustment mechanism of the upper bracing member is substantially in alignment with the cutout hole of the mid bracing member upon engagement with the mid bracing member; wherein the width adjustment mechanism of the lower bracing member substantially offsets the cutout hole of the cutout hole of the mid bracing member upon engagement with the mid bracing member.

In some embodiments, each of the bracing members of the modular brace comprises elastic fabric material; wherein each of the sensor module comprises a rigid housing that provides structural retention; wherein a number of the sensor module that couples the upper bracing member is less than a number of the sensor module that couples the lower bracing member.

In some embodiments, the external add-on member comprises physiological sensors in the rigid hollow housing.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A wearable apparatus for a multimedia interaction system, configured to interface a plurality of groups of skin-mounted sensor pads over a body part of a wearer, the wearable apparatus comprising:
a modular brace structurally separated from the plurality of groups of skin-mounted sensor pads, the modular brace comprising:
a plurality of groups of orienting slots configured to maintain an intra-group formation within one group of the plurality of groups of skin-mounted sensor pads, and
a width adjustment mechanism arranged between separated groups of the plurality of groups of orientating slots and configured to allow an inter-group distance adjustment between the plurality of groups of skin-mounted sensor pads over the body part of the wearer; and
a plurality of sensor modules configured to be detachably coupled to the plural groups of skin-mounted sensor pads through the plural groups of orienting slots in the modular brace, wherein
the plurality of sensor modules comprises physiological sensing circuits for wirelessly communicating with the multimedia interaction system.

2. The wearable apparatus of claim 1,
wherein the modular brace defines an inward surface and an outward surface, and
wherein the inward surface of the modular brace is configured to press over the plurality of groups of skin-mounted sensor pads without stickiness to maintain a positioning orientation of the plurality of groups of skin contact pads over the body part of the wearer.

3. The wearable apparatus of claim 2,
wherein the modular brace comprises an upper bracing member, a mid-bracing member, and a lower bracing member,
wherein the upper bracing member, the mid-bracing member, and the lower bracing member are engageable and structurally detachable from one another; and
wherein each of the upper bracing member, the mid-bracing member, and the lower bracing member is self-retainable over the body part of the wearer.

4. The wearable apparatus of claim 3,
wherein the mid-bracing member is provided with a cutout hole configured to retain over a hinge joint of the wearer to establish an orientation reference for the upper bracing member and the lower bracing member, and
wherein the mid-bracing member is provided without the plurality of groups orienting slots.

5. The wearable apparatus of claim 4,
wherein at least one of the upper bracing member and the lower bracing member includes a pliant strap body arranged along a length of the upper bracing member or the lower bracing member and defining a longitudinal axis, the pliant strap body comprising:
a pair of fasteners arranged at two ends of the pliant strap body along the longitudinal axis, and configured to engage each other to form a loop that wraps around the body part of the wearer, and
a pad retaining section arranged between the pair of fasteners and the plurality of groups of orientating slots are distributed on the pad retaining section, and
wherein the pad retaining section is provided with the width adjustment mechanism along the longitudinal axis and configured to enable the inter-group distance adjustment between the plurality of groups of groups of skin-mounted sensor pads along the longitudinal axis.

6. The wearable apparatus of claim 5,
wherein at least one of the upper bracing member and the lower bracing member includes an interconnecting member configured to engage the mid-bracing member, thereby retaining a separation distance between the plurality of groups of skin-mounted sensor pads in a direction normal to the longitudinal axis, and
wherein the interconnecting member is provided with a length adjustment mechanism that enables an adjustment of the separation distance.

7. The wearable apparatus of claim 6,
wherein at least one of the width adjustment mechanism and the length adjustment mechanism is provided with visual positioning marks arranged between the plurality of groups of orientating slots.

8. The wearable apparatus of claim 5,
wherein the width adjustment mechanism of the upper bracing member is in alignment with the cutout hole of the mid bracing member when the upper bracing member is engaged with the mid bracing member, or
wherein the width adjustment mechanism of the lower bracing member offsets the cutout hole of the cutout hole of the mid bracing member when the lower bracing member is engaged with the mid bracing member.

9. The wearable apparatus of claim 3,
wherein each of the upper bracing member, the mid-bracing member, and the lower bracing member comprises an elastic fabric material,
wherein each of the plurality of sensor modules comprises a rigid housing that provides structural retention, and wherein a number of the plurality of sensor modules that couples the upper bracing member is less than a number of the plurality of sensor modules that couples the lower bracing member.

10. The wearable apparatus of claim 9,
wherein the plurality of sensor modules comprises physiological sensors in the rigid housing.

11. A wearable apparatus for retaining a plurality of groups of skin contact pads over a body part of a wearer, the wearable apparatus comprising:
a modular brace structurally separated from the plurality of groups of skin contact pads, the modular brace comprising:
a plurality of groups of orienting slots configured to maintain an intra-group formation within one group of the plurality of groups of skin contact pads, and
a width adjustment mechanism arranged between separated groups of the plurality of groups of orientating slots and configured to enable an inter-group distance adjustment between the plurality of groups of skin contact pads over the body part of the wearer; and
a plurality of external add-on members configured to detachably couple the plurality of groups of skin contact pads through the plurality of groups of orienting slots in the modular brace.

12. The wearable apparatus of claim 11,
wherein the modular brace comprises an upper bracing member, a mid-bracing member, and a lower bracing member,
wherein the upper bracing member, the mid-bracing member, and the lower bracing member are engageable and structurally detachable from one another; and
wherein each of the upper bracing member, the mid-bracing member, and the lower bracing member is self-retainable over the body part of the wearer.

13. The wearable apparatus of claim 12,
wherein the mid-bracing member is provided with a cutout hole configured to retain over a hinge joint of the wearer to establish an orientation reference for the upper bracing member and the lower bracing member, and
wherein the mid-bracing member is provided without the plurality of groups of orienting slots.

14. The wearable apparatus of claim 13,
wherein at least one of the upper bracing member and the lower bracing member includes a pliant strap body arranged along a length of the upper bracing member or the lower bracing member and defining a longitudinal axis, the pliant strap body comprising:
a pair of fasteners arranged at two ends of the pliant strap body along the longitudinal axis, and configured to engage each other to form a loop that wraps around the body part of the wearer, and
a pad retaining section arranged between the pair of fasteners and the plurality of groups of orientating slots are distributed on the pad retaining section, and
wherein the pad retaining section is provided with the width adjustment mechanism along the longitudinal axis and configured to enable the inter-group distance adjustment between the plurality of groups of skin contact pads along the longitudinal axis.

15. The wearable apparatus of claim 14,
wherein the width adjustment mechanism of the upper bracing member is in alignment with the cutout hole of the mid-bracing member when the upper bracing member is engaged with the mid-bracing member, or
wherein the width adjustment mechanism of the lower bracing member offsets the cutout hole of the cutout hole of the mid-bracing member when the lower bracing member is engaged with the mid-bracing member.

16. The wearable apparatus of claim 15,
wherein the width adjustment mechanism is provided with visual positioning marks arranged between the plurality of groups of orientating slots.

17. The wearable apparatus of claim 14,
wherein at least one of the upper bracing member and the lower bracing member includes an interconnecting member configured to engage the mid-bracing member, thereby retaining a separation distance between the plurality of groups of skin contact pads in a direction normal to the longitudinal axis, and
wherein the interconnecting member is provided with a length adjustment mechanism that enables an adjustment of the separation distance.

18. The wearable apparatus of claim 12,
wherein each of the upper bracing member, the mid-bracing member, and the lower bracing member comprises an elastic fabric material, and
wherein each of the plurality of external add-on members comprises a rigid housing that provides structural retention.

19. The wearable apparatus of claim 18,
wherein the plurality of external add-on members comprises physiological sensors in the rigid housing.

20. The wearable apparatus of claim 11,
wherein the modular brace defines an inward surface and an outward surface, and
wherein the inward surface of the modular brace is configured to press over the plurality of groups of skin contact pads without stickiness to maintain a positioning orientation of the plurality of groups of skin contact pads over the body part of the wearer.

* * * * *